(12) United States Patent
Pan et al.

(10) Patent No.: US 6,272,200 B1
(45) Date of Patent: Aug. 7, 2001

(54) FOURIER AND SPLINE-BASED RECONSTRUCTION OF HELICAL CT IMAGES

(75) Inventors: Xiaochuan Pan; Patrick Jean La Riviere, both of Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/362,484

(22) Filed: Jul. 28, 1999

(51) Int. Cl.⁷ ........................................................ A61B 6/03

(52) U.S. Cl. ............................................. 378/15; 378/901

(58) Field of Search ................................. 378/4, 15, 901

(56) References Cited

U.S. PATENT DOCUMENTS

5,406,479 * 4/1995 Harman ..................................... 378/7
6,108,575 * 8/2000 Besson .................................. 600/425

* cited by examiner

*Primary Examiner*—David V. Bruce
(74) *Attorney, Agent, or Firm*—Welsh & Katz, Ltd.; A. Sidney Katz; Jon P. Christensen

(57) ABSTRACT

A method and apparatus are provided for reconstructing a set of CT images from helical CT data. The method includes the steps of receiving the helical CT data and generating a set of fan-beam sinograms at equally spaced longitudinal positions. The method further includes the steps of estimating a set of parallel-beam sinograms from the generated set of fan-beam sinograms and reconstructing the CT images using a parallel beam reconstruction algorithm.

42 Claims, 9 Drawing Sheets

Z (UNITS OF DETECTOR WIDTH)

Z (UNITS OF DETECTOR WIDTH)

FOURIER AND SPLINE-BASED RECONSTRUCTION OF HELICAL CT IMAGES

The U.S. Government has a paid-up license in this invention and the right in limited circumstances to require the patent owner to license others on reasonable terms as provided for by the terms of Grant #CA70449 as awarded by the National Institute of Health.

FIELD OF THE INVENTION

The field of the invention relates to computed tomography and more particularly to the generation of images in helical computed tomography (CT).

BACKGROUND OF THE INVENTION

There are currently three principal approaches to volumetric imaging in CT. In conventional volumetric CT, the object is scanned one slice at a time with a single row of detector elements and is translated only between slice acquisitions. In single-slice helical CT, the object is translated continuously while the x-ray tube rotates. The ratio of the object-translation distance per 360° revolution of the source to the longitudinal width of the detector array is known as the pitch; it is usually chosen to be near 1. Finally, in multi-slice helical CT, the source illuminates several rows of detector elements at once in a small-angle cone-beam geometry. As in single-slice helical CT, the object is translated while the x-ray source rotates, although pitches much higher than 1 are feasible in this arrangement.

Helical CT offers a number of clinical benefits. The numerous advantages of helical CT have allowed it to displace conventional CT as the test of choice in many clinical situations and allowed for the development of new imaging protocols that were not even possible with conventional CT. Perhaps the most important advantage of helical CT is its high-volume-scanning speed. Helical CT can scan entire organ volumes in a single breathhold, thereby eliminating the acquisition gaps that can arise in conventional CT when anatomic structures do not realign precisely after breathing. Helical CT is thus particularly recommended for studies of the thorax, which suffers most from such respiratory motion and misregistration. Moreover, much thoracic imaging is performed with contrast agents, and the superior volume scanning speed of helical CT allows it to capture the phase of peak organ opacification, whereas conventional CT, if it can be used at all, will necessarily capture some slices only as the contrast agent dilutes. On this account, multi-slice helical CT provides clear advantages over even single-slice helical CT.

One contrast-enhanced study first made possible by helical CT is CT angiography (CTA), where the need for high temporal resolution is even greater than in organ contrast studies. Once again, multi-slice helical CT provides clear temporal resolution advantages over single-slice helical CT, but this is one area that could still benefit from improved temporal resolution. Faster scanning allows for more precise tracking of the injected bolus and thus allows for a shorter bolus to be used in the first place. This, in turn, reduces the chance that surrounding venous structures and perfused tissue will enhance before the scan is complete.

Additional clinical benefits of helical CT include its ability to perform retrospective overlapping slice reconstructions, which can facilitate nodule detection in the lung and liver. These studies in particular benefit from improved longitudinal resolution and reduced noise, which facilitate the detection of small lesions. Helical CT also makes possible the generation of multiplanar reformats from reconstructed volumes that do not contain any of the gaps and misalignments commonly found in conventional CT volumes, although these reformats would still benefit from improvements in resolution and noise isotropy.

There are a number of current approaches to longitudinal interpolation in helical CT. One group of these is referred to as the 180LI and 360LI approaches. Unlike conventional volumetric CT, which yields a complete set of projections for each slice being imaged, helical CT yields projections acquired at different longitudinal positions along the object. The general strategy for reconstructing slice images in helical CT is to interpolate the needed projection views from the measured projections. Helical CT reconstruction approaches differ primarily in their choice of interpolation approach and the amount of data used in the interpolation. In single-slice helical CT, most current approaches opt for linear interpolation. The simplest way of using the data is the 360LI approach, in which linear interpolation is applied to projections 360° apart and located on either side of the slice in question. The 180LI approach exploits the redundancy of fan-beam data to generate a second helix of data prior to performing linear interpolation to obtain the desired projections.

Another approach involves the use of weighting functions. These interpolations can, of course, be performed in the straightforward way to yield transverse sinograms that can be reconstructed by fan-beam algorithms, but an alternative approach has been developed that provides a framework for more general and sophisticated strategies. The approach entails multiplying the measured helical projection data by a carefully designed weighting function prior to reconstruction by CBP. While naturally accommodating the 360LI and 180LI approaches, which in this context are known as full scan with interpolation and half-scan with interpolation, the strategy has spawned a number of other approaches, such as the underscan, half-scan, and helical extrapolative (HE) approaches.

Another approach involves the use of wide-kernels. In single-slice CT, approaches that use a wider interpolation kernel have been developed, such as an approach in which the interpolation weights minimize a worst-case normalized maximum error magnitude criterion. It was shown that this yields improved images over 360LI approaches, although Crawford and King later found little advantage to this approach over the 180LI and HE approaches. More recently, Hu and Shen introduced an approach incorporating longitudinal filtration into the weighting procedure, resulting in the use of more measured data in the estimation of each transverse sinogram. They did find advantages to this approach, particularly in the much greater flexibility it afforded for choosing the desired tradeoff between slice broadening and noise levels.

Other approaches have been developed for multi-slice helical CT. While also seeking to interpolate needed projection views from measured ones, multi-slice helical CT reconstruction must contend with the more complex sampling pattern of the measured projections in this geometry. A variety of interpolation strategies have been propose, many based on linear interpolation. It should be noted that whereas the small cone-beam angle encountered in multi-slice helical CT would seem to present an additional reconstruction challenge, existing approaches often disregard it because the longitudinal detector collimation (~2–10 mm) is very small compared to the source-to-detector distance (~1000 mm) and thus the cone angle is very small.

The physical characteristics of current approaches to longitudinal interpolation in helical CT must be considered. One of these characteristics is the aliasing and resolution properties of helical CT.

The physical characteristics of existing approaches to helical CT have been studied extensively. The longitudinal resolution of any volumetric CT reconstruction is naturally limited by the finite longitudinal collimation of the detector rows. Not surprisingly, the longitudinal interpolation step in helical CT leads to an additional broadening of slice profiles relative to conventional volumetric CT. However, there has long been a belief expressed in the literature that the ability to perform retrospective reconstruction at any longitudinal position offsets this broadening and, in fact, leads to longitudinal resolution superior to that in conventional volumetric CT. This belief has been bolstered by studies of SSP and MTF curves at the isocenter, performed with radially symmetric objects.

Yen et al. have clarified the situation by performing a detailed analysis of sampling patterns and aliasing effects in conventional and single-slice helical CT. They showed that a peculiar aliasing cancellation effect occurs only at the isocenter of a radially symmetric object, and that a fair comparison of helical and conventional CT and among different helical CT interpolation approaches should result in the examination of aliasing and resolution effects at other transverse positions. Indeed, according to their analysis, only at the isocenter is it even meaningful to speak in terms of continuous SSP and MTF curves that implicitly ignore the effects of aliasing. Such curves do, however, offer some measure of the transmission of principal, unaliased frequencies, and are thus still of some use for comparing different interpolation approaches in helical CT. For example, the superior SSP and MTF properties of the 180LI approach over the 360LI approach at the isocenter are reflected at other transverse positions by a decrease in the relative magnitude of the aliasing effect in the 180LI case. This ability to reduce the relative magnitude of aliasing effects will be referred to loosely as an improvement in longitudinal resolution, and improvements in longitudinal resolution that do not entail unacceptable increases in noise levels are always useful.

In an effort to improve resolution, some researchers have investigated the application of deconvolution to the reconstructed volume in order to compensate for the blurring introduced by the finite longitudinal collimation of the detector rows and the subsequent interpolation. Another desirable goal is to achieve more isotropic resolution, that is, to decrease the change in the relative magnitude of the aliasing effect as a function of transverse position and also to achieve comparable resolution longitudinally and transversely.

Noise properties are another consideration. The choice of interpolation approach also affects noise levels in the reconstructed volume, with approaches employing wiser interpolation kernels generally resulting in lower noise levels than those employing shorter interpolation kernels. Noise levels have been studied analytically and empirically by a number of investigators. Most significantly, Hsieh has examined the spatial distribution of noise levels in helical CT volumes reconstructed with linear interpolation approaches and found it to be non-stationary relative to that in conventional CT, a situation that can impede the detection of low-contrast lesions and lead to artifacts in MIP images. The nonstationarity of the noise has its root in the fact that the application of linear, and indeed most, interpolation approaches to samples corrupted by white noise leads to interpolated curves that have a nonstationary variance, with maxima at the points corresponding to measured samples and minima midway between such samples. Whereas Hsieh proposed a postprocessing approach to mitigate the appearance of the artifacts, an interpolation approach that eliminated the very source of the artifacts would clearly be desirable.

In addition to the possibility of artifacts, noise properties have important implications for patient dose, tube loading, and tube life. Specifically, a reconstruction approach that can reduce noise without significantly compromising accuracy allows scans to be acquired at lower tube currents, which reduces patient radiation exposure, allows for longer scans with fewer tube cooling delays, and extends tube life. Indeed, Hu and Shen have pointed out the benefits of approaches that allow noise levels to be controlled in more flexible ways than are allowed by approaches based on simple linear interpolation.

Other artifacts may also be present. Other artifacts that must be considered when one examines helical CT interpolation approaches include stair-step artifacts, partial-volume artifacts, and, in the multi-slice case, cone-beam artifacts. Stair-step artifacts can be seen in reformatted longitudinal slices containing inclined surfaces. The continuous boundaries of such artifacts take on a staircase appearance in these images. The origins of the artifacts and strategies for suppressing them were investigated in the context of linear interpolation approaches. Partial-volume artifacts in helical CT have the same origin as in conventional CT—the presence of significant axial variations in attenuation within a collimated beam—although helical CT provides some means for suppressing them. Cone-beam artifacts arise in multi-slice helical CT when techniques that ignore the small cone angle are used. These artifacts are seen principally around the spine and within blood vessels that have been fitted with stent-grafts. It is worthwhile to study the effect of any novel interpolation approach on these types of artifacts.

Finally, transverse reconstruction algorithms may be considered. Because the output of any helical CT interpolation procedure is a set of transverse fan-beam sinograms, the choice of reconstruction algorithm clearly affects the final image quality. Two principal approaches exist for fan-beam reconstruction. The first, direct CBP, involves convolving each projection with an appropriate filter, followed by a distance-dependent backprojection. This distance-dependent backprojection is computationally intensive and, it can be shown, liable to amplify noise and numerical errors in the outer regions of the reconstructed image, although it is generally very accurate in the central regions of the image. The second approach involves rebinning the fan-beam data into a parallel-beam sinogram and then employing parallel-beam filtered backprojection (FPB) to reconstruct the image. The rebinning entails a two-dimensional (2D) interpolation. While this approach is generally more efficient than direct CBP, the use of bilinear interpolation can compromise image accuracy. Accordingly, a need exists for an improved method of reconstructing CT images from helical CT data.

SUMMARY

Figure 1:
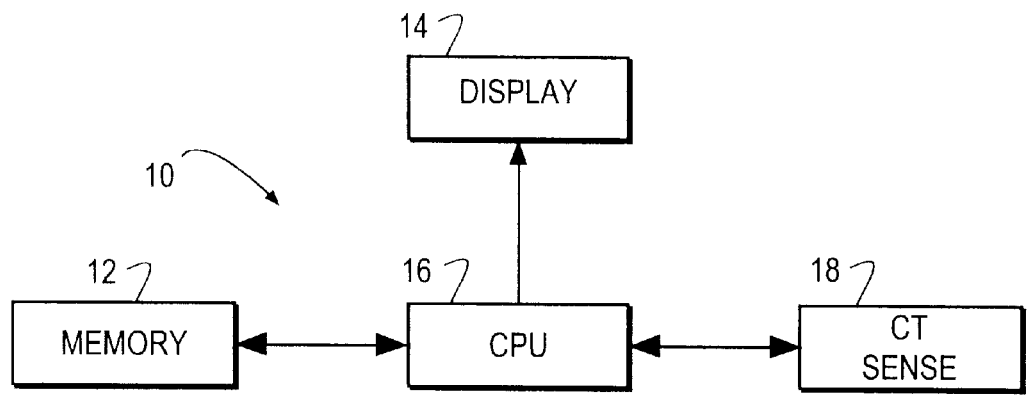
FIG. 1 is a block diagram of a system for reconstructing helical CT data under an illustrated embodiment of the invention.

The broad objective of the invention is to develop, implement, and evaluate novel Fourier- and spline-based approaches to the image-reconstruction problems encountered in single- and multi-slice helical computed tomography (CT). Theoretical and empirical studies indicate that the approaches provide longitudinal resolution and noise properties superior to those of existing approaches. These physical advantages have obvious implications for the detection of focal lesions, as in pulmonary scanning for the detection of lung nodules, because improved resolution and noise properties often translate into improved diagnostic accuracy. Moreover, in dynamic studies employing contrast agents, such as CT angiography (CTA), these advantages can be traded off for improved temporal resolution, which allows more precise bolus tracking and thus greater image contrast.

The areas developed herein include a number of considerations. The first area includes the development of a Fourier-based longitudinal interpolation approach for helical CT.

A Fourier-based approach to longitudinal interpolation in helical CT has been developed which exploits the Fast Fourier Transform (FFT) and the Fourier shift theorem to generate from the helical projection data a set of fan-beam sinograms corresponding to equispaced transverse slices. In the single-slice case, the approach exploits the Fourier shift theorem to align the samples for all view angles at a specified set of equispaced longitudinal positions, thus yielding a set of transverse fan-beam sinograms. In the multi-slice case, the approach also invokes the Fourier shift theorem, but with a novel twist to deal with the aliasing necessarily present in the samples from any one detector row.

An efficient implementation of this approach enabling greater noise suppression and resolution enhancement is also discussed. In particular, because the approach operates in the Fourier space of the longitudinal samples, the application of various Fourier-domain filters for noise control is discussed, as well as Fourier-domain deconvolution techniques to compensate for the finite longitudinal collimation of the detector rows and other system blurring effects. Extensions of the approach which takes explicit account of the cone-beam geometry in multi-slice helical CT will also be discussed.

A second approach to longitudinal interpolation in helical CT is based on fitting splines to the measured data. A spline is a piecewise polynomial curve that has many favorable numerical and statistical properties. Most significantly for the application to multi-slice CT, splines can naturally accommodate non-uniformly spaced measurement points without great algorithmic complexity or computational burden.

A cubic-spline interpolation approach for both single- and multi-slice helical CT is developed. In addition, the use of smoothing splines is examined for noise and, by extension, dose reduction, with the degree of smoothing determined automatically from the data by a technique known as generalized cross validation (GCV). Our spline-based approach, also offers a natural means of compensating for the finite longitudinal collimation of the detector rows. Such an extension is developed and the results assessed as to whether it affords significant resolution improvements over the basic model. Extensions of this approach that take explicit account of the cone-beam geometry in multi-slice helical CT are also examined. Our spline-based approach differs in important ways, to be discussed below, from the spline approach investigated by some investigators, and found wanting by others.

Optimal methods for the exploitation of redundant fan-beam information are developed. It is well known that the minimum angular range required in a fan-beam acquisition for exact image reconstruction is $\pi+2\gamma_m$, where $\gamma_m$ is the fan angle. By extension, an acquisition over $2\pi$ necessarily contains redundant information that, in helical CT, can be exploited to reduce the effective sampling interval in the longitudinal direction: this is the basis of the existing 180LI approach. However, the additional samples do not necessarily align exactly with the measured angular views. Thus, interpolation may be required in the longitudinal direction. Also. the additional samples do not necessarily fall midway between the existing samples, but rather lead to a non-uniform sampling pattern. In the discussed methods, we develop optimal means for addressing these issues and thus for exploiting the redundant information in both the Fourier- and spline-based approaches. Making use of this information leads to further improvements in image resolution.

Novel fan-beam reconstruction algorithms are also developed and evaluated. Regardless of the longitudinal interpolation approach used in helical CT, the result of this interpolation is a set of fan-beam sinograms corresponding to transverse slices. Image reconstruction can proceed by use of conventional algorithms such as convolution backprojection (CBP), but the effect of using novel hybrid algorithms is also discussed. It is shown that these hybrid algorithms are more efficient and less susceptible to noise and numerical errors than is CBP. Properties of the hybrid algorithms such as resolution, noise, and sensitivity to inconsistent data are also discussed. Currently, these hybrid algorithms may be applied to data acquired over the angular range $[0, 2\pi]$. Similar hybrid algorithms for short-scan data acquired over the angular range $[0, \pi+2\gamma_m]$ are also contemplated.

The physical characteristics and clinical-task performance of the proposed approaches, with respect to existing approaches are also evaluated. The evaluation of physical characteristics, such as aliasing, resolution, and noise properties is important for characterizing and comparing the fundamental performance of reconstruction approaches. The first physical characteristic of interest is an approach's response to and effect on longitudinal aliasing, which is a complex but significant issue in helical CT. Closely related to studies of aliasing effects is the study of a system's longitudinal resolution, which at least at the isocenter, can be characterized by a slice sensitivity profile (SSP) as well as a longitudinal modulation transfer function (MTF). These are computed analytically and verified empirically for both the Fourier and spline-based approaches used in concert with the novel hybrid reconstruction algorithms and compared to those of currently used linear interpolation approaches. Our results indicate superior resolution performance for the new approaches.

We also consider, through analytic derivation and extensive numerical simulation, the noise properties of the approaches, which theory predicts will be superior to those of the linear approaches, where noise non-stationarity has been shown to lead to artifacts in maximum intensity projection (MIP) of reconstructed volumes. The ability to suppress noise without sacrificing accuracy also makes possible the reduction of patient dose. We also consider the sensitivity of the approach to data inconsistencies caused by patient motion, physiologic motion, contrast-agent flow, and partial-volume effects.

Although the study of the physical characteristics of a particular approach can be a powerful predictor of clinical performance, ultimately, one is interested in the actual impact of the approach on the performance of clinically meaningful tasks. For this reason, we also conduct evaluations of the approaches in the face of clinically relevant data, obtained through numerical simulations, physical-phantom studies, and the use of existing patient studies. Tasks include the detection of small lesions, such as pulmonary nodules, or low-contrast pathologic abnormalities such as diffuse parenchymal disease in the liver. The proposed and existing approaches will be compared on the basis of both model observer studies employing the channelized Hotelling observer, which fairly accurately reproduces the results of human observer studies, and genuine human observer studies conducted by use of the receiver operating characteristic (ROC) methodology.

The primary significance of the proposed approaches is that they preserve all of the inherent advantages of helical CT available when linear interpolation is used while improving physical characteristics such as aliasing response, longitudinal resolution, and noise properties, with little or no additional computational burden. Such improvements have a number of clinical implications. First, improved longitudinal resolution improves the diagnostic accuracy in studies involving the detection of small, low-contrast objects such as lung nodules. Second, the ability to reduce or control image noise levels in optimal ways can be exploited either for improving image quality for a given patient radiation exposure or for reducing patient exposure while holding image quality constant. Reduced exposure also reduces the burden on overworked x-ray tubes. Third, the approaches are expected to have better isotropic noise and resolution properties than do existing approaches, which would improve the quality of multiplanar reformats generated from reconstructed volumes.

Perhaps the most significant clinical benefit of the proposed approaches, however, would be the ability to trade off the resolution and noise improvements for improved temporal resolution. The time taken to scan a given volume can always be reduced by increasing the pitch. However, increasing the pitch leads to degradations in resolution and increase in noise levels. Reconstruction algorithms with improved resolution and noise properties over existing approaches could generate images of similar quality from data obtained at higher pitches. As was mentioned above, this would particularly benefit CTA, where improved temporal resolution translates directly into improved bolus tracking and thus improved image contrast.

The Fourier-based approach offers a number of specific physical benefits. For example, the Fourier-based approach is particularly computationally efficient because it exploits the FFT and can simultaneously generate all of the required projections through the use of the zero-padding and Fourier shift techniques. Moreover, for functions that are sampled in accordance with the Nyquist criterion, the interpolation kernel in this approach is theoretically exact. This assumption is reasonable given the low-pass filtering effect of the finite detector collimation, and we have shown in theoretical and empirical resolution studies that the Fourier-based approach has resolution properties superior to those of equivalent linear interpolation approaches. Moreover, theoretical and empirical studies of the noise properties of functions interpolated by means of Fourier-based approaches have indicated that it does not lead to the nonstationary noise levels obtained using linear and other interpolation approaches and thus would be expected to eliminate at their source the MIP artifacts reported by Hsieh. Finally, because the Fourier-based approach operates in the Fourier domain of the projections, it should be possible to incorporate deconvolution compensating for the finite longitudinal collimation of the detector rows into the reconstruction process rather than as a separate postprocessing step as is currently done. Owing to the theoretically optimal interpolation kernel, there is, in principle, no need to compensate for interpolation blurring in postprocessing.

The spline-based approach also offers a number of specific physical benefits. For example, the spline-based approach shares many of the advantages of the Fourier-based approach. The approach can be made computationally efficient if one takes advantage of the fact that the longitudinal sampling pattern at each view angle is identical up to an overall shift. Thus the matrices relating spline coefficients to the measured data, which depend only on the relative distribution of sampling points, need only be computed once. The spline coefficients at each view angle can then be used for calculating projections at arbitrary longitudinal positions. Spline interpolation is generally more accurate than linear interpolation, and our preliminary studies have indicated that it, too, leads to improved resolution performance compared to the approaches based on linear interpolation.

The noise properties are also theoretically superior to those of linear interpolation, particularly when the possibility of using smoothing splines, with their favorable statistical properties, is considered. Like the Fourier-based approach, the spline-based approach has the ability to compensate for the finite longitudinal collimation of the detector rows in the course of the interpolation, rather than as a separate post-processing step. Finally, it should be mentioned that the reason for investigating splines at all when their properties, however favorable, are not as theoretically optimal as those of the Fourier-based approach is that splines may prove to be more robust in practice than the Fourier-based approach, which is potentially sensitive to violations of the assumption that the functions being interpolated are sampled in accordance with the Nyquist condition.

The novel fan-beam algorithm also provides specific physical benefits. The final aspect of the work discussed herein is the use of hybrid algorithms that were developed for reconstruction of the transverse slices from fan-beam sinograms. These algorithms lead to improvements in both computational efficiency and noise properties without sacrificing accuracy and increasing patient dose. As the algorithms involve a sophisticated rebinning strategy, they avoid the computational burden and noise and aliasing amplification of the distance-dependent backprojection in direct fan-beam CBP without the sacrifice in accuracy entailed in using bilinear interpolation to shift from fan-beam to parallel-beam coordinates. Moreover, they accomplish this in a way that provides for theoretically optimal noise reduction. This noise reduction can be exploited either to improve the signal-to-noise ration (SNR) in images acquired at usual clinical dose levels or to reduce patient dose while maintaining a constant SNR. Moreover, the algorithms are expected to lead to more stationary noise levels in reconstructed images, a property that can enhance the detectability of subtle signals.

Under illustrated embodiments described below, a method and apparatus are provided for reconstructing a set of CT images from helical CT data. The method includes the steps of receiving the helical CT data and generating a set of fan-beam sinograms at equally spaced longitudinal positions. The method further includes the steps of estimating a set of parallel-beam sinograms from the generated set of fan-beam sinograms and reconstructing the CT images using a parallel beam reconstruction algorithm.

DETAILED DESCRIPTION OF A PREFERRED EMBODIMENT

FIG. 1 is a block diagram of a system 10 for processing CT images in accordance with an illustrated embodiment of the invention. As shown, a central processing unit (CPU) 16 may collect helical CT data through use of a CT sensing device 18. The CT sensing device may include an X-ray source and detector array physical supported by a gantry. The gantry may be used for rotation and translation of the source and detector devices.

Once helical CT data is collected, it may be stored in a memory 12, or processed directly. Processing of images may be performed in the CPU 16 and presented on the display.

Figure 2:
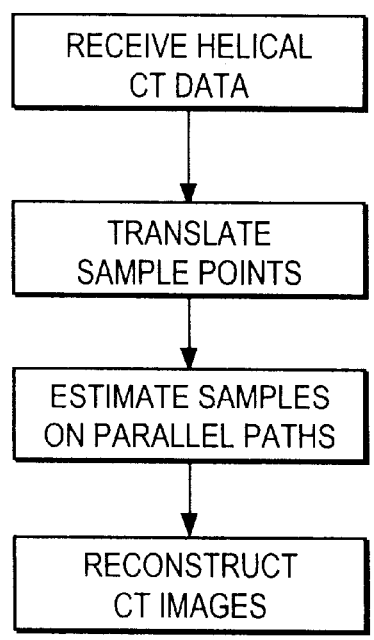
FIG. 2 is a flow chart that may be used by the system of FIG. 1.

FIG. 2 shows a flow chart of processing steps used by the system of FIG. 1. Reference shall be made to FIG. 2 as appropriate to an understanding of the invention.

Turning now to the Fourier based approach, an overview will be provided of the processing methods and results. Following the discussion of the Fourier based approach, a spline-based approach will be considered.

Figure 3:
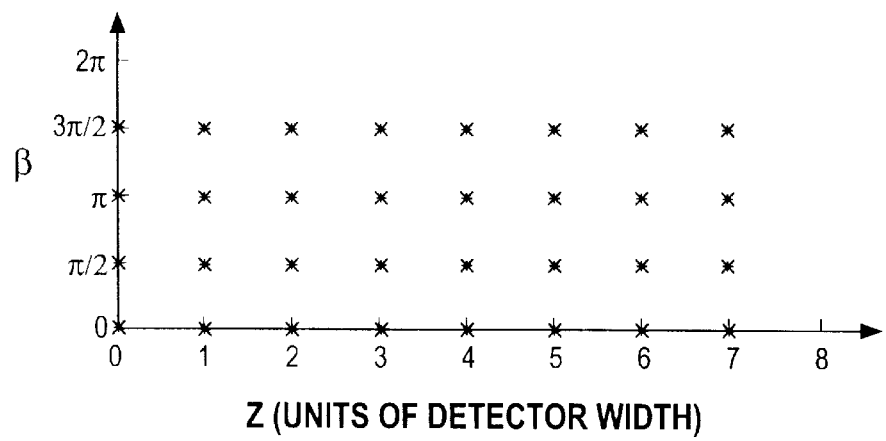
FIG. 3 is a sampling pattern that may be used by the system of FIG. 1.

The Fourier-based approach may be implemented in its basic form, without extensions allowing for apodization windows and deconvolution. To understand the development of the Fourier-based approach, it is important to appreciate the longitudinal sampling patterns encountered in conventional and helical CT. In volumetric CT, the transverse fan-beam projection data $p(\gamma,\beta,z)$ can be interpreted as a three-dimensional (3D) function in the space $\{\gamma,\beta,z\}$, where $\gamma$ denotes the angle between the projection line and the center of the fan beam, $\beta$ denotes the angular position of the source, and z denotes the longitudinal position of the slice being projected. In practice, one always works with samples of $p(\gamma,\beta,z)$ on a finite grid $\{\gamma,\beta,z\}(i=0, \ldots, j=0, \ldots, M-1, k=0, \ldots, N R-1)$ of the $\{\gamma,\beta,z\}$ space. The number of longitudinal samples is given by the product of N, the number of detector rows, and R, the number of revolutions. In conventional CT, the grid is generally uniform in all three dimensions. Thus, for all fixed $\gamma$, the sampling pattern of $p(\gamma,\beta,z)$ in the $\{\beta,z\}$ subspace is as shown in FIG. 3.

Figure 4:
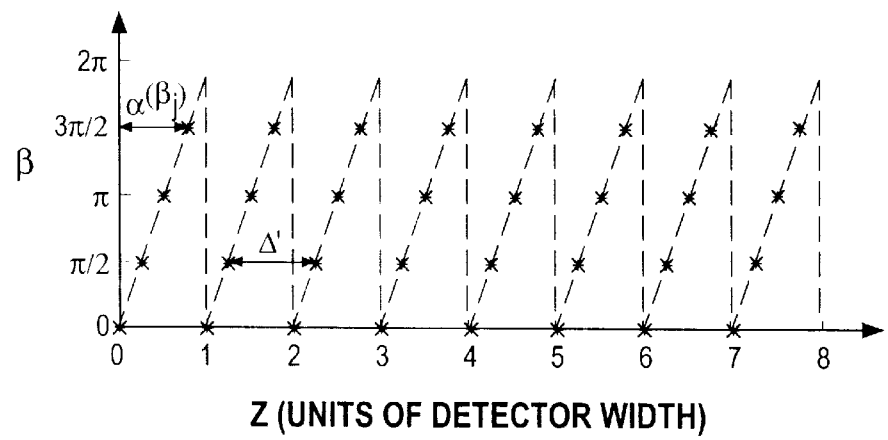
FIG. 4 is a sampling pattern of a single slice helical CT that may be used by the system of FIG. 1.

In single-slice helical CT, however, the sampling pattern is more complicated. Because the object is being translated continuously, each of these projections is acquired at a different longitudinal position z. Thus, for a fixed $\gamma$, the sampling of $p(\gamma,\beta,z)$ in the $\{\beta,z\}$ subspace is as shown in FIG. 4. Notice that the sampling pattern at each projection view is uniform and simply shifted relative to the sampling pattern at other projection views. Our strategy, then, is to exploit the Fourier shift theorem to translate the longitudinal sampling grid at each view angle in such a way that the samples for all view angles are aligned at a specific set of equally spaced longitudinal positions, thus yielding a set of single-slice, fan-beam sinograms. In a sense, the sampling pattern of FIG. 4 is transformed by the CPU 16 into the sampling pattern of FIG. 3. It is perhaps worth stating explicitly that the shifting the sampling grid is not the same as sifting the sample values, that would be like reconstructing directly from the raw helical data without interpolating at all. The Fourier-based approach is a form of interpolation that determines new sample values at the shifted sample points.

Figure 5:
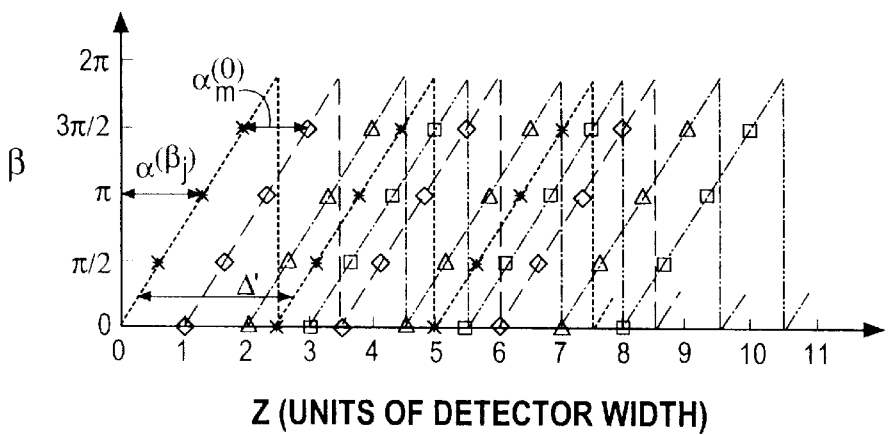
FIG. 5 is a sampling pattern of a multi-slice helical CT that may be used by the system of FIG. 1.

In multi-slice helical CT, if the acquisition pitch is equal to the number N of detector rows, the strategy employed in the single-slice case can be carried over directly because the resulting sampling pattern is not uniform, as shown in FIG. 5, although it is, of course, not wholly random either. It is, in fact, periodically non-uniform, comprising N interleaved sets of uniform samples. The strategy is again to exploit the Fourier shift theorem to align the sampling grids, although because of the aliasing present in any one detector row's samples, a system of N frequency-space equations must be solved by the CPU 16 to achieve this alignment.

Figure 6:
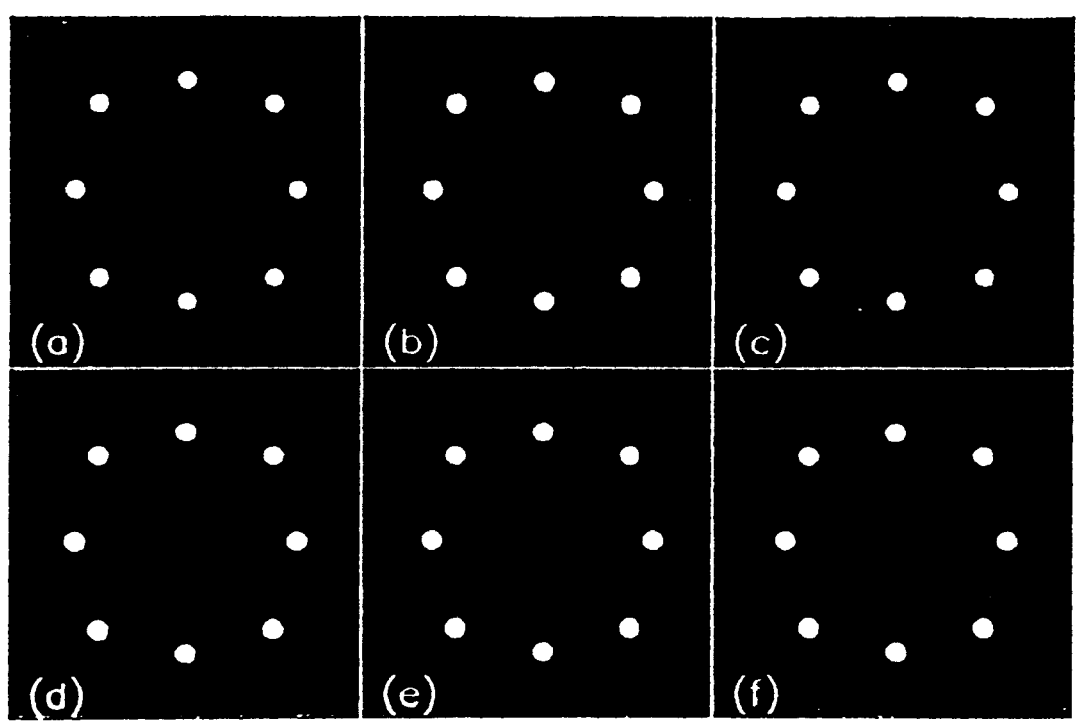
FIG. 6 depicts an image that may be reconstructed by the system of FIG. 1.

A set of preliminary empirical results with the basic Fourier-based approach may now be considered. In order to illustrate the use of the Fourier-based approach for single- and multi-slice helical CT, a numerical phantom identical to one used by Taguchi and Aradate may be generated, consisting of a set of eight identical spheres of radius 10 mm arrayed on a circle of radius 100 mm. Single- and multi-slice (4 detector rows) helical CT sinograms may be generated assuming a detector collimation of 2 mm and a focal length of 600 mm for a variety of pitches. Images may be reconstructed by the CPU 16 using both the basic Fourier-based approach and the conventional 360LI approach for single- and multi-slice data. In FIG. 6, a transverse slice is shown located 5 mm from the center of one set of spheres for each reconstruction approach and for pitch 1 in the single-slice geometry and pitch 4.5 in the multi-slice geometry. It can be seen that none of the images display the sort of artifacts seen by Taguchi and Aradate in their multi-slice helical CT reconstruction based on straightforward linear interpolation.

In order to compare the longitudinal resolution performance of the proposed FFT-based approach to that of the 360LI approach, SSPs of these approaches may be computed by applying them to a single- and multi-slice helical CT projections of an object representing a longitudinal impulse function. A full characterization of longitudinal resolution would take into account sampling and aliasing effects at a variety of transverse positions, but, as pointed out in the discussion above, MTF measurements along the isocenter do correlate with the relative performance of different approaches at off-isocenter positions. The same geometry as described above may be used, but this time to scan a coin phantom of radius 10 mm and thickness 0.2 mm placed at the center of rotation. Slice images with a 0.1. mm reconstruction increment may be reconstructed and the average value computed in an ROI of radius 10 mm for each slice to obtain the SSP.

Figure 7:
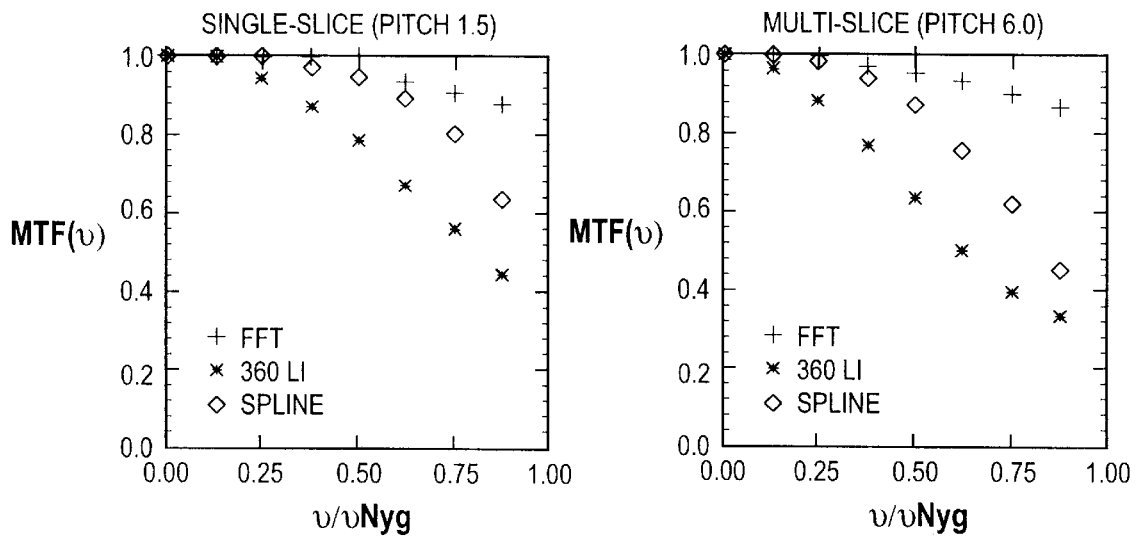
FIG. 7 depicts samples of a longitudinal MTF for single and multi-slice helical CT.

Although it is traditional in helical CT to compare resolution performance by comparing the relative widths of SSPs, the rather different functional forms of the linear-interpolation and Fourier-based SSPs makes this impractical and somewhat meaningless. In this situation, the MTF, which is simply the modulus of the Fourier transform (FT) of the SSP, provides a more meaningful comparison, and MTFs may be computed by calculating the modulus of the discrete FT (DFT) of the SSP samples. This may be done for a variety of pitches for both single- and multi-slice geometries and the Fourier-based approach has been found to yield higher MTFs than did the 360LI approach, indicating that the Fourier-based approach has superior longitudinal resolution properties. FIG. 7 shows a representative result: samples of the MTFs for a single-slice geometry operating at pitch 1.5 and a multi-slice geometry operating at pitch 6.0.

It is well known that the longitudinal resolution performance of approaches based on linear interpolation is improved when one exploits the redundancy of fan-beam data acquired over 360° to increase the effective longitudinal sampling density; this is the basis of the 180LI approach. This redundancy can be exploited in our Fourier-based approach as well, and an efficient way of incorporating it is provided.

An overview of the basic spline-based approach will now be considered. The spline-based approach may be implemented by the CPU 16 in its basic form, without the extensions allowing for smoothing and integral splines. the approach, which is quite different from the Fourier-based approach, is to fit a continuous curve-a cubic spline-on the set of longitudinal samples $p(\gamma, \beta, z)$ at each $\gamma_i$ and $\beta_j$. These curves may then be resampled at any z in order to generate fan-beam sinograms at arbitrary longitudinal positions. Splines have very attractive numerical and computational properties, and their use has been investigated for a variety of limited-data problems commonly encountered in medical imaging, in particular for few-view tomography. Suppose, for notational simplicity, that we have sample $g(z_k)$ of a one-dimensional function $g(z)$ at points $z_k, k=0, \ldots, NR-1$, where N and R denote the number of detector rows and revolutions, respectively. A spline $\hat{g}(z)$ can be represented by $$\hat{g}(z) = a_k' + b_k'(z-z_k) + c_k'(z-z_k)^2 + d_k'(z-z_k)^3, \quad (1)$$

for $z \in [z_k, z_{k+1}]$. The $z_k$ need not be uniformly spaced, a feature of splines makes them particularly well-suited for the multi-slice helical CT problem.

Fitting a spline is tantamount to finding the coefficients of $a_k'$, $b_k'$, $c_k'$, and $d_k'$ subject to measurement, continuity, and boundary conditions. Applying these conditions entails performing a set of linear operations on the data; thus, if the measured samples $g(z_k)$ are represented as a vector y having NR elements, the vectors of the coefficients can be found from y through matrix multiplications a'=Ay, b'=By, c'=Cy, and d'=Dy, where the matrices A, B, C, and D can be deduced and depend only on the spacing of the measurement locations $z_k$. In both single- and multi-slice helical CT, the sampling pattern is identical for all $\gamma\gamma_i$ and $\beta_j$, just shifted at different $\beta_j$ so that the matrices A, B, C, and D need be computed only once, a feature that contributes to the computational efficiency of the approach. once computed, the matrices can simply be used for multiplying the longitudinal samples $p(\gamma, \beta, z)$ at each $\gamma_i$ and $\beta_j$ to yield coefficients of $a_k'$, $b_k'$, $c_k'$, and $d_k'$ that may be used to evaluate $p(\gamma, \beta, z)$ at arbitrary z and thus to generate fan-beam sinograms at arbitrary z. This approach to fitting interpolating splines differs from the use of a four-point spline kernel for interpolation by discrete convolution in that the effective kernel in the present case is wider and smoother than approximate four-point spline kernels and less likely to give rise to the sort of longitudinal ringing artifacts reported by others. Moreover, as we shall discuss below, the present framework is considerably more flexible in that it allows naturally for smoothing and integral-model splines.

The preliminary empirical results provided by the system 18 using the basic spline-based approach may be considered. The single- and multi-slice spline-based approaches may be applied to the same helical data used in the studies of the Fourier-based approach. Transverse images of the ball-phantom are shown in FIG. 6 and MTF curves are shown in FIG. 7. The approach is seen to yield transverse slices of visual quality comparable to that of slices obtained with the Fourier-based or linear interpolation approaches, indicating that the spline-based approach has resolution properties superior to those of the linear interpolation approach.

An analytic study of resolution in the Fourier-based approach may be performed as follows. A thorough study of the longitudinal resolution at an arbitrary transverse position in a helical CT volume reconstruction must take account of aliasing effects. However, at the isocenter of radially uniform objects, an aliasing cancellation phenomenon makes aliasing negligible and thus makes possible a continuous-domain analysis in terms of SSPs and MTFs. Moreover, comparing such curves for different interpolation approaches does offer some measure of the relative magnitude of the aliasing effect expected at off-isocenter points. In order to make such a comparison, we have derived the isocenter SSP for the single-slice Fourier-based approach, which is given by $$s(z) = \frac{1}{Pw} \sin c\left(\frac{z}{Pw}\right) * \tilde{f}(z) \quad (2)$$

where * denotes a convolution, $\sin c(x) = \sin(\pi x)/(\pi x)$, P is the pitch, w is the longitudinal collimation, and $\tilde{f}(z)$ is the periodic extension of the detector response, which is usually taken to be rectangular.

It is not surprising that the expression for the SSP takes the form of a convolution, because it does so also for the single-slice linear interpolation approach, although two significant differences emerge. The first is that the convolution involves the periodic extension of the detector response function rather than just the function itself. This arises because the FFT implicitly assumes that the samples it operates on are samples of a periodic function. The second difference is that the form of the convolving function is very different: it is a sin c function in this case, whereas for linear interpolation approaches it is a triangle function. The form of the convolver has important consequences for the longitudinal resolution properties of reconstructed volumes. Whereas SSPs for linear interpolation approaches are usually compared directly by plotting them and examining their relative widths, the very different functional forms of these curves in the Fourier-, spline- and linear-based approaches makes this SSP comparison impractical and somewhat meaningless.

A set of MTF calculations may be obtained for comparison. It is more meaningful to compare longitudinal MTFs, which are defined to be the moduli of the FTs of SSPs, although, to be most meaningful, such a comparison should also include the effects of a finite reconstruction interval. As others have pointed out, the isocenter SSP $s_1(z)$, when using a reconstruction interval lw, is given by the convolution of the theoretical, dense-slice SSP, $s(z)$, and a low-pass filtering function (1/lw)sin c(z/lw). For the Fourier-based approach to single-slice helical CT, the MTF can be shown to be $$MTF(v) = |\text{rect}(Pwv)\sin c(wv)\text{comb}(RPwv)| \quad (3)$$

where $$\text{comb}(x) = \sum_{m=-\infty}^{\infty} \delta(x - mx)$$

and rect is the rectangle function. The rect(Pwv) factor means that the MTF falls to zero above the frequency v=Pw/2, which is not surprising because v=Pw/2 is the Nyquist frequency for samples spaces of Pw, which is the sampling interval in single-slice helical CT. The factor comb (NPwv) means that the MTF is not continuous, but rather passes discrete frequencies spaces by intervals 1/RPw. This is a consequence of using the FFT. Finally, the factor of greatest interest is sin c(wv), which is the envelope of the MTF. For comparison, the MTF of the 360LI approach can be shown to be $$MTF_{360LI}(v) = |\text{rect}(lwv)\sin c^3(wv)|. \quad (4)$$

Figure 8:
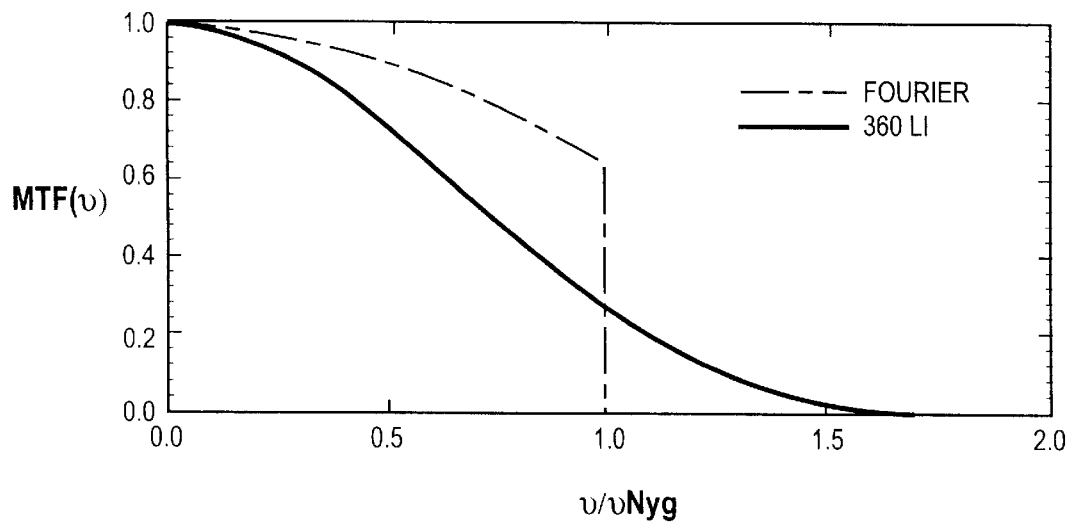
FIG. 8 depicts isocenter MTFs for Fourier-based and 360LI interpolation reconstruction.

Plotting the two together in FIG. 8, we see that the Fourier-based approach has a uniformly higher MTF than does the 360LI approach when extended out to the Nyquist frequency. Thus, so long as the longitudinal functions being interpolated satisfy the Nyquist criterion at least approximately-that is, they have little or no spectral energy beyond the Nyquist frequency of the samples-the Fourier-based approach provides isocenter resolution superior to that of the 360LI approach, and thus less relative aliasing error away form the isocenter.

The noise properties in the Fourier- and spline-based approaches may be considered analytically next. For the Fourier-based approach, an expression may be derived for the variance in a volume reconstructed with the Fourier-based approach and CBP for single-slice helical CT. The noise in the measured samples may be assumed to be uncorrelated and the variance more or less constant as a function of longitudinal position for fixed γ and β. This is a reasonable assumption because variance is related to the inverse of measured counts, which tend to vary most strongly due to patient thickness, which, in turn, tends to vary little as a function of longitudinal position for fixed γ and β.

One researcher has pointed out that to understand the noise-related artifacts that arise in helical CT, it is helpful to consider the point-by-point ratio of the helical CT slice variance to the conventional CT slice variance for fixed z. Our derivation indicates that this ratio is a constant equal to 1 for the basic Fourier-based approach and less than 1 if high-frequency components are explicitly suppressed in an effort to reduce noise, as will be discussed below. In contrast, one source has shown that for linear interpolation approaches, the ratio varies substantially as a function of position, affecting low-contrast detectability and giving rise to so called zebra artifacts in MIPs of the reconstructed volumes. This stationary noise property of the Fourier-based approach is one of its principal advantages.

The spline-based approach may be considered next. It is possible in principle to carry out a similar analysis for the spline-based approach, although the resulting expression would be dependent on the matrices A, B, C, and D (see above) and would thus not lend itself to simple interpretation and comparison to the conventional CT slice variance.

Figure 9:
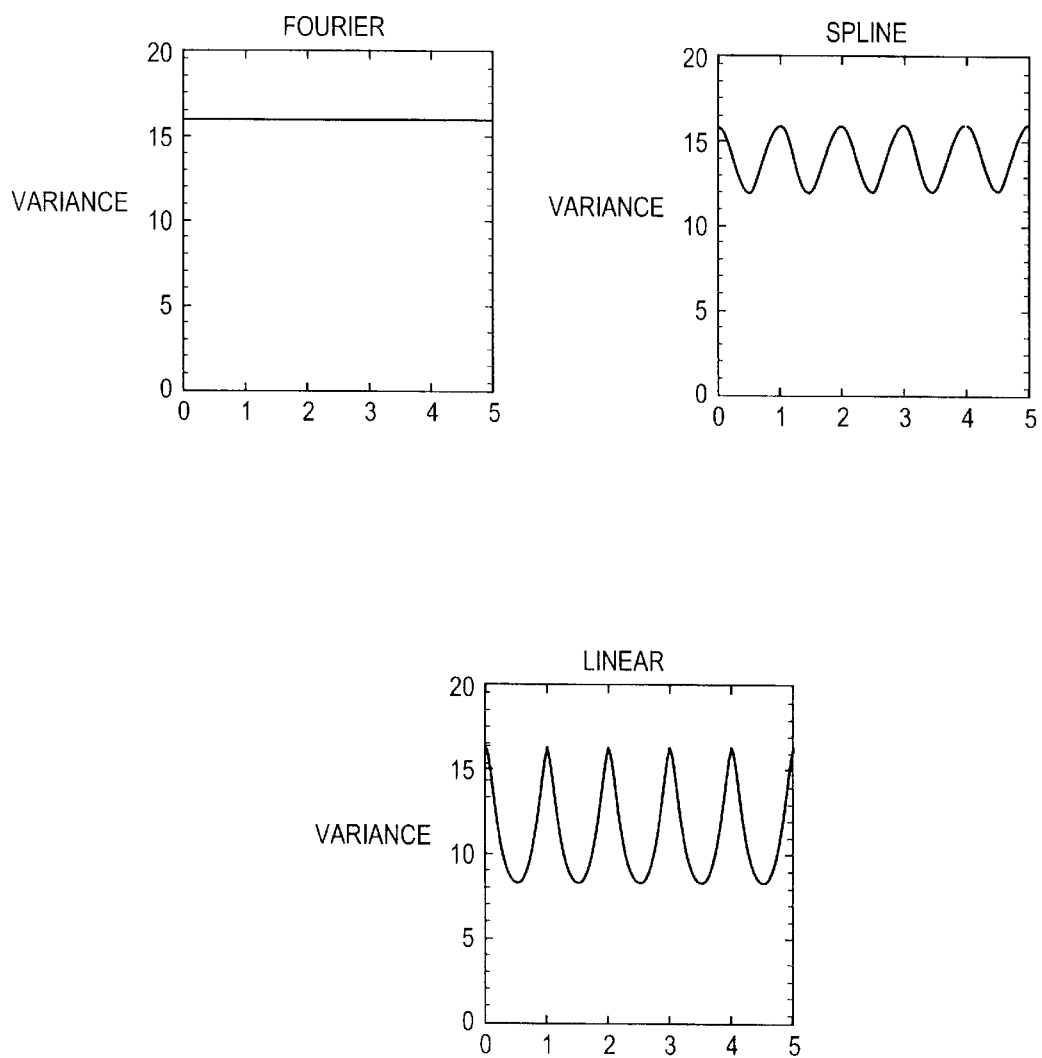
FIG. 9 depicts variance curves of the system of FIG. 1.

However, the noise properties of helical CT volumes reconstructed with the spline-based approach can be inferred and compared to those of the Fourier-based and linear interpolation approaches by consideration of the simpler case of the variance of a 1D function interpolated from samples contaminated by uncorrelated white noise. The results of analytic predictions of the variance of such a curve interpolated by use of Fourier-based, spline-based, and linear interpolation approaches are shown in FIG. 9.

The Fourier-interpolated curve is seen to have a constant variance, which explains the constant ratio of the variance in a helical volume obtained with the Fourier-based approach to that in a conventional CT volume. The linearly interpolated curve, on the other hand, is seen to have a highly non-stationary variance, which is maximal at the positions of the measured samples and falls to half that level midway between measured samples. This behavior is the source of the highly nonstationary quality of noise in helical CT volumes reconstructed with linear interpolation and the artifacts that arise in MIPs of such volumes. The spline-interpolated curve, while not having an entirely nonstationary variance, does not fluctuate as widely as does the linearly interpolated curve. Thus, helical CT volumes obtained by the spline-based approach display a much milder form of the nonstationarity observed by one researcher for the linear interpolation approaches, and it is possible that the nonstationarity could be eliminated entirely with the use of smoothing splines.

The novel fan-beam reconstruction algorithms will be considered next. A class of so-called hybrid algorithms may be developed that involve estimating a parallel-beam sinogram from the fan-beam data prior to reconstruction by parallel-beam filtered backprojection (FBP). These hybrid algorithms differ from conventional fan-to-parallel rebinning algorithms in two principal ways. First, explicit use is made of the redundant information contained in fan-beam acquisition over 2π to obtain two estimates of the parallel-beam sinogram. In the absence of noise and other variability, the estimates are mathematically identical, but in the presence of the noise they contain statistically complementary information. By setting the parallel-beam sinogram used for reconstruction equal to a weighted combination of these two estimates, one can achieve a bias-free reduction of variance in the reconstructed image.

Second, whereas conventional fan-to-parallel rebinning approaches use explicitly 2D interpolation, such as bilinear interpolation into two 1D interpolations. One of these (between angular coordinates) is accomplished by use of a form of the Fourier-shift strategy; the other (between bin coordinates) is accomplished by use of linear or, in a sophisticated implementation, spline interpolation. These hybrid algorithms have three principal advantages over CBP: they are more computationally efficient, they are less likely to amplify noise and numerical errors, and they generate images with more stationary noise properties.

Figure 10:
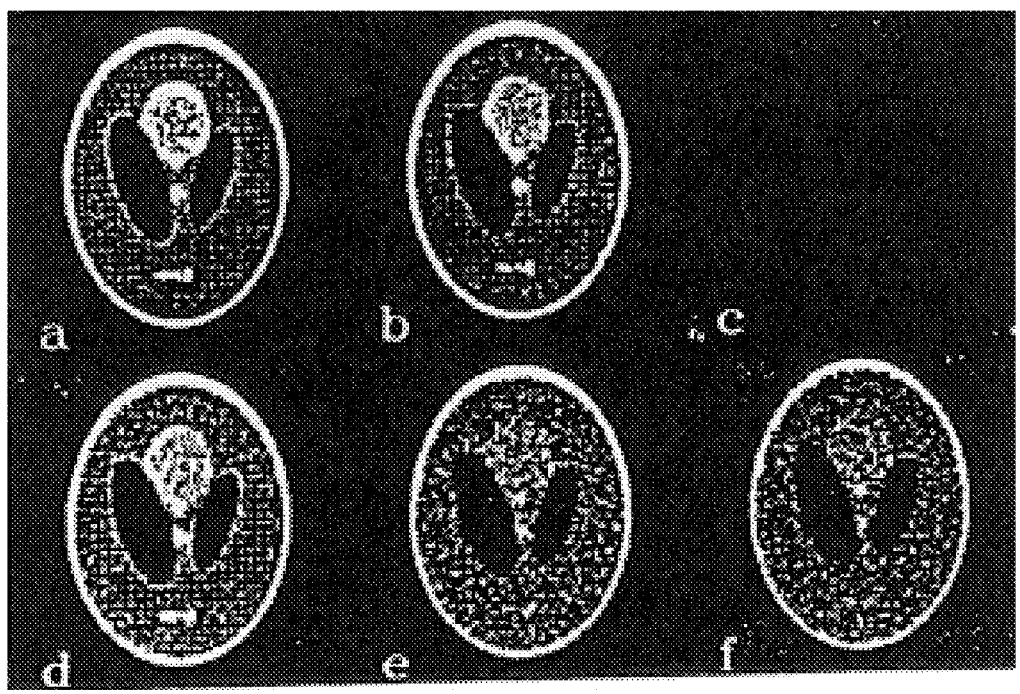
FIGS. 10a–f depicts original and reconstructed images of a Shepp-Logan phantom that may be reconstructed using the system of FIG. 1.
FIG. 10g depicts image variance of FIGS. 10a–g along the y-axis calculated from 1500 images by use of CBP (dashed line) and the hybrid algorithm.

Preliminary results are as follows. To study the properties of these hybrid algorithms, a numerical Shepp-Logan phantom may be used, as shown in FIG. 10a. Using one of the hybrid algorithms and CBP, reconstructed images from computer-simulated noiseless projections of the phantom may be obtained. The results are shown in FIGS. 10b and 10c. The strong artifacts in the outer region of the image in FIG. 10c somewhat obscure the structure of the Shepp-Logan phantom, indicating that the conventional CBP algorithm is sensitive to the aliasing effect of finite sampling. In FIG. 10d, we thus display only the portion of the image array that contain the phantom.

Figure 10G:
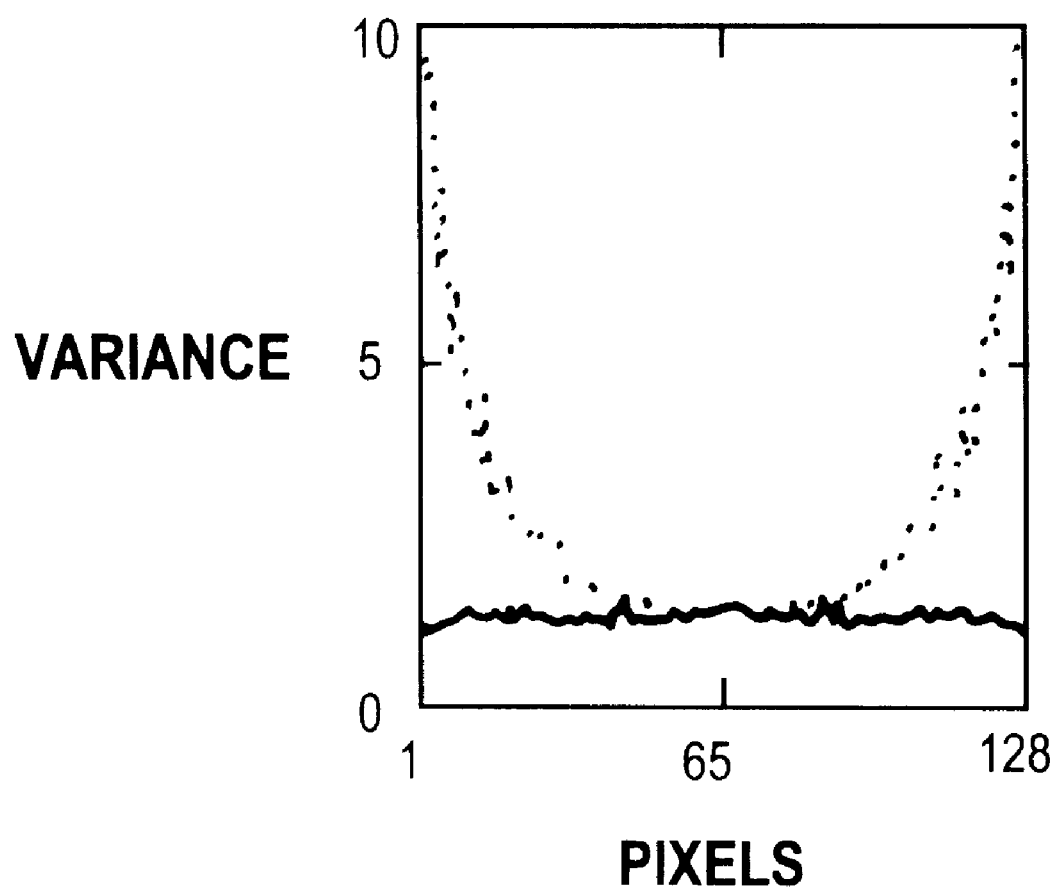

Using the same hybrid algorithm and CBP, images from computer-simulated noisy data may be reconstructed, and the results are shown in FIGs. 10e and 10f. Again, we only display the central portion of the images obtained with CBP. The image obtained by CBP appears noticeably noisier than that obtained with the hybrid algorithm. We also generated 1500 sets of noisy fan-beam sinograms that contained stationary, white Gaussian noise. Employing the hybrid algorithm and CBP to reconstruct 1500 images from these noisy sinograms, we then calculated the empirical variances in the reconstructed images, which are shown in FIG. 10g. This figure shows quantitatively both that hybrid algorithm yields a lower variance than does CBP and that it yields more stationary noise than does CBP.

A Fourier-based longitudinal interpolation approach for helical CT may also be developed. Uniform sample shifting may be considered first. The Fourier-based approach depends on the ability to compute uniform, arbitrarily shifted samples of a 1D function from single or multiple sets of differently shifted uniform samples of the function. Let $f_{a_0}(z) \equiv f(z+a_0)$ denote the function $f(z)$ shifted by an arbitrary distance $a_0$. Suppose that we have a set of uniform samples. $g_{a_0}(z)$, of $f_{a_0}(z)$ having sampling interval $\Delta'$. The task we wish to consider is the estimation of uniform samples of $f(z)$, given the samples $g_{a_0}(z)$. For now, we assume that the desired samples also have sampling interval $\Delta'$ and have offset $a_0=0$, although more general cases can easily be accommodated.

Let $G_{a_0}(\upsilon)$ and $F(\upsilon)$ be the FTs of $g_{a_0}(z)$, of $f(z)$, respectively. It can be shown that $$G_{a_0}(v) = \frac{1}{\Delta'} \sum_{n=-\infty}^{\infty} e^{j2\pi(v-\frac{n}{\Delta'})a_0} F\left(v - \frac{n}{\Delta'}\right), \quad (5)$$

where $\upsilon$ is the frequency conjugate to z. If we assume that $f(z)$ is bandlimited to $$\frac{1}{2\Delta}$$

and that $\Delta'=\Delta$, the replications $$F\left(v - \frac{n}{\Delta'}\right)$$

for different values of n do not overlap. Thus, in the frequency range $$|v| < \frac{1}{2\Delta}$$

Eq. 5 reduces to $$F(v)=\Delta' e^{-j2\pi v a_0} G_{a_0}(v) \quad (6)$$

and $F(\upsilon)$ is uniquely determined by $G_{a_0}(\upsilon)$. In a discrete implementation, Eq. 6 provides a method for obtaining a set of uniform samples of $f(z)$ given a set of shifted uniform samples $g_{a_0}(z)$: take a DFT of $g_{a_0}(z)$, multiply the result by $\Delta' e^{-j2\pi v a_0}$, and take an inverse DFT. Because one only makes use of FFT and simple multiplication operations, this approach for obtaining a set of samples of $f(z)$ is extremely efficient.

This approach may now be applied to single-slice helical CT. Use of this approach for single-slice helical CT turns on recognizing in FIG. 4 that for each measured $\gamma_i$ and $\beta_j$, one can regard the projection data as a 1D function of z, of which we have R samples of spacing $\Delta'$ offset from the origin $z=0$ by a distance $a^{(\beta_j)}$. The approach described above can be used as follows. Given helical CT samples $p(\gamma_i,\beta_j,z_k)$, we take a 1D FFT with respect to $z_k$ of the samples at each pair of $\gamma_i$ and $\beta_j$. In accordance with Eq. 6, the resulting frequency-space samples, which lie precisely in the range $$|v| \leq \frac{1}{2\Delta'},$$

are multiplied by the phase factor $\Delta' e^{-j2\pi v a^{(\beta_j)}}$ and an inverse 1D FFT performed. The effect is to shift the sampling grid in the spatial domain such that all the samples within each of the R revolutions line up at the same z values, in this case at $z=k\Delta'$ for $k=0,\ldots,R-1$. Manipulation of the phase factors allows realignment on any set of equispaced planes. Moreover, by zero-padding the FFT of the samples by an integer factor, one can increase the density of the estimated longitudinal planes by the same factor. At this point, 2D fan-beam algorithms can be applied to reconstruct the images.

A Fourier-based approach may be used for multi-slice helical CT. Periodic non-uniform sample shifting will be considered first.

An interesting case arises when $f(z)$, still assumed to be bandlimited to $$\frac{1}{2\Delta},$$

is sampled at larger intervals $\Delta'=N\Delta$, where $N>1$ is an integer. The samples may still be offset from the origin. In this case, the spectral replications F $$F\left(v - \frac{n}{\Delta'}\right)$$

in Eq. 5 for different values of n do overlap, and $F(v)$ can no longer be uniquely determined from $G_{a_0}(v)$ or by extension from a single set of samples $g_{a_0}(z)$. However, $F(v)$ can uniquely determined if one has N sets of such samples $g_{a_0}(z)$ with different offsets $a_m$.

In the range $$\frac{1}{2\Delta} - \frac{1}{N\Delta} \leq v \leq \frac{1}{2\Delta},$$

it can be shown that $G_{a_0}(v)$ is given by $$G_{a_m}(v) = \frac{1}{\Delta'} \sum_{n=0}^{N-1} e^{j2\pi(v-\frac{n}{\Delta'})a_m} F\left(v - \frac{n}{\Delta'}\right), \quad (7)$$

for $m=0,\ldots N=1$. This is a set of N linear equations that can be solved for the F $$F\left(v - \frac{n}{\Delta'}\right),$$

which correspond to different segments of F(v). In the discrete case, Eq. 7 allows us to solve for different portions of the DFT of f(v) and thus can be used for obtaining samples of f(v). Again, this approach is extremely efficient because it involves FFT and multiplication operations as well as the solution of a small (N is typically 4) system of linear equations. Also, it can be shown that Eq. 7 becomes Eq. 6 when N=1.

This approach may be applied to multi-slice helical CT. Use of the approach in multi-slice helical CT can be understood by examination of FIG. 5. In this more general case, we need to consider separately the N sets of longitudinal samples of $p(\gamma_i,\beta_j,z)$ at each pair of $\gamma_i$ and $\beta_j$. Each set is uniformly spaced with sampling interval $\Delta'$ and is offset from the origin by the distance $$a_m^{(\beta j)} = a_m^{(0)} + a^{(\beta j)}, \tag{8}$$

where $a_m^{(0)}$ is the distance between the mth detector and the first (m=0) detector and $a^{(\beta j)}$ is as before. The interval $\Delta'$ will in general be several times larger than in the single-slice case.

The approach is implemented as follows. Given helical CT samples $p(\gamma_i,\beta_j,z_k)$ from detector m, we take a 1D FFT with respect to $z_k$ of the samples at each pair of $\gamma_i$ and $\beta_j$ to obtain samples of $G_{a_m}^{(\beta j)}(v)$. Whereas this FFT would usually be understood to yield frequencies in the range $$\frac{-1}{2N\Delta} \le v \frac{1}{2N\Delta}$$

(for $\Delta'=N\Delta$)owing to the implicit periodicity of the aliased spectrum these also stand in for the frequencies in the range $$\frac{1}{2\Delta} - \frac{1}{N\Delta} \le v \frac{1}{2\Delta}$$

of interest. Equation 7 is then solved to yield samples of the N segments of $F^{(\beta j)}(vV)$. The segments obtained are appropriately ordered, and an inverse FFT is taken to yield samples of $p(\gamma_i,\beta_j,z_k)$ With the proper choice of phases, these samples can be made to align at the same arbitrary, equispaced z positions for all $\gamma_i$ and $\beta_j$. At this point, fan-beam algorithms can be applied to reconstruct the slice images.

Apodization windows may be used for noise suppression in the Fourier-based approach. For example, it is well known that at high spatial frequencies, noise tends to overwhelm the signal in many imaging modalities. Thus, one common approach to noise suppression is to multiply the FT of the noisy function by an apodization filter that suppresses high spatial frequencies. Because the Fourier-based approach to helical CT already involves computing the FFT of the longitudinal samples at each $\gamma_i$ and $\beta_j$, in order to carry out the sample-shifting strategy, this noise reduction strategy can be applied at virtually no additional computational cost.

The simplest apodization window is a rectangular window that explicitly sets the highest frequency components to 0 while not altering lower-frequency components. If only the 2K+1 lowest frequency components of the longitudinal transforms are preserved, where K<N R/2, then for stationary white noise, it can be shown that the overall noise level is reduced by the constant factor $$\frac{2K+1}{NR}$$

relative to that in conventional CT. As simple as it is, this filter is in principle optimal if the underlying function is bandlimited to K, for in this situation the underlying function is oversampled and the superfluous samples can be used to reduce noise without introducing bias.

If the underlying function is not in fact bandlimited to K, however, the sharp truncation of this filter can lead to ringing and other aliasing artifacts in the interpolated function that generally negate any advantages gained by the noise suppression. For this reason, it is often desirable to use a more smoothly varying apodization window that suppresses some lower frequencies while descending smoothly to zero beyond a prespecified cutoff. The use of a number of such windows may be considered, including the well-known Hanning, Hamming, and Butterworth windows as well as novel windows of our own design that account more explicitly for expected noise properties in helical CT.

Fourier-domain deconvolution may be used for resolution enhancement in the Fourier-based approach. Means of compensating explicitly for the blur introduced by the finite longitudinal collimation of the detector elements may be examined while controlling noise in the Fourier-based approach. Specifically, the use of Fourier-domain deconvolution approaches may be provided that can be applied directly to the longitudinal FFT samples that are already obtained at each $\gamma_i$ and $\beta_j$ in order to carry out the sample-shifting strategy. Fourier-domain deconvolution approaches, such as Wiener filtering, have been employed to compensate for detector and interpolation blur in helical CT with linear interpolation, but in that situation deconvolution was applied in a postprocessing step to longitudinally reformatted, reconstructed images. This entails the additional computational burden of computing forward and inverse longitudinal FFTs of the entire reconstructed volume. Our strategy will take advantage of the fact that our Fourier-based approach already requires the computation of longitudinal FFTs of the projection data, which will enable us to correct directly for the detector blur present in those samples through Wiener filtering.

In the Wiener filtering approach, the longitudinal FFT samples may be multiplied by Wiener filters of the form $V(v)=T(v)[\tau+T(v)^2]^{-1}$, where $T(v)$ is FT of the blur kernel and $\tau$ is free parameter that governs the tradeoff between resolution recovery and noise suppression. This formulation of the Wiener filter implicitly assumes that the noise in the longitudinal samples is stationary and uncorrelated, a fairly reasonable assumption in this context.

The approach may be extended the explicit cone-beam geometry. The Fourier-based approach to the multi-slice case has implicitly assumed so far that the geometry of multiple, parallel fan beams projecting precisely transverse planes. In truth, the multi-slice projection planes are slightly oblique, because the detectors and source form a small-angle cone-beam geometry. The cone angle is extremely small with the detector collimation (~2–10 mm) being very small compared to the source-to-detector distance (~1000 mm), and therefore ignoring it is generally a good assumption. However, in some circumstances, cone-beam artifacts do arise that can be dispelled only by explicitly accounting approaches that can explicitly account for this geometry while still preserving the advantages of the proposed Fourier-based approach.

Cone-beam reconstruction is a theoretically intriguing and practically important problem, and great advances have been made in this area in the last 15 years. A number of investigators have developed reconstruction algorithms for non-planar scanning configurations, including the helical scanning configuration. In principle, any of these algorithms can be used for performing a fully 3D reconstruction. However, despite efforts to improve their efficiency, the computational load of these algorithms is generally prohibitively heavy, and certainly would be for the large datasets encountered in helical CT. Moreover, the algorithms lack the numerical stability of 2D algorithms such as FBP.

Because the cone angle is so small in multi-slice helical CT, it is a good candidate for the application of more efficient, approximate cone-beam algorithms. Defrise et al. recently developed such an approach in the context of 3D PET, whereby they effectively rotate parallel-beam projections in tilted planes into projections in transverse planes. Given the projections in transverse planes, one can reconstruct a stack of 2D images to form the desired 3D images, thus avoiding performing a computationally intense 3D reconstruction.

In multi-slice helical CT, the cone-beam projections in planes that are not perpendicular to the longitudinal z axis can be interpreted as fan-beam projections in tilted planes. We propose to extend Defrise's approach to the fan-beam case in order to convert these tilted fan-beam projections into transverse fan-beam projections. This will enable us still to use our proposed Fourier-based approach for the image reconstruction, thus preserving the computational and other advantages of our approach. In order to accomplish this goal, this extended Defrise approach may be used to correct for the obliqueness in each detector's projections individually. Strategies may be developed to correct for the obliqueness in all N detector rows simultaneously. Optimal means for exploiting the redundant information in this process may also be developed.

A spline-based longitudinal interpolation approach may also be provided for helical CT. A spline-based approach for single- and multi-slice helical CT may be considered first.

Because splines can naturally accommodate non-uniform samples, the same essential approach will be used in both the single- and multi-slice cases. The first step is to compute the basic longitudinal sampling pattern that arises at all $\gamma_i$ and $\beta_j$ (the relative position of the points in the sampling grid is the same at all $\gamma_i$ and $\gamma_j$; there is just an overall shift of the grid for different $\beta_j$). This sampling pattern will be denoted $z_k$, $k=0,\ldots NR-1$, where we can assume that $z_0=0$ without loss of generality. This sampling pattern is uniform with an interval equal to Pw in single-slice helical CT, and it is generally non-uniform and dependent on the pitch and detector width in multi-slice helical CT. This pattern is then used for determining the matrices A, B, C, and D relating the spline coefficients to the measured data. As the matrices depend only on the differences $z_{k+1}-z_k$, they need be computed only once for all $\gamma_i$ and $\beta_j$, despite the overall shift of the sampling pattern for different $\beta_j$. For each $\gamma_i$ and $\beta_j$, we define a vector $$p^{(\gamma_i,\beta_j)} \equiv (p(\gamma_i,\beta_j,z_0), p(\gamma_i,\beta_j,z_1), \ldots, p(\gamma_i,\beta_j,z_{NR-1}))^T, \quad (9)$$

having N R elements, where, in the multi-slice case, the longitudinal samples $p(\gamma_i,\beta_j,z_k)$, considered as a function of $z_k$, are obtained by appropriate interleaving of the samples from each of the detector rows. Then, through matrix multiplications, $$a'=Ap^{(\gamma_i,\beta_j)}, b'=Bp^{(\gamma_i,\beta_j)}, c'=Cp^{(\gamma_i,\beta_j)}, \text{ and } d'=Dp^{(\gamma_i,\beta_j)}, \quad (10)$$

the vectors of spline coefficients may be obtained at each $\gamma_i$ and $\beta_j$.

To generate a fan-beam sinogram at arbitrary z, the following expression may then be evaluated, for all $\gamma_i$ and $\beta_j$, $$p(\gamma_i,\beta_j,z)=a_k'+b_k'(z-z_k^{(\gamma_i,\beta_j)})+c_k'(z-z_k^{(\gamma_i,\beta_j)})^2+d_k'(z-z_k^{(\gamma_i,\beta_j)})^3, \quad (11)$$

where $$z_k^{(\beta_j)} = z_k + \frac{Pw}{2\pi}\beta_j,$$

and k is the index of the interval such that $$z \in \left[z_k^{(\beta_j)}, z_{k+1}^{(\beta_j)}\right].$$

Like the Fourier-based approach, the spline-based approach may be implemented in IDL. The approach will be implemented as flexibly as possible in C.

Smoothing splines may be used for noise suppression in the spline-based approach. The spline-fitting approach discussed in the previous section can accommodate smoothing splines just as well as interpolating splines. An interpolating spline is one that is constrained to pass through the measured sample values. This is of course desirable if the measured samples are known exactly, but in practice they are always corrupted somewhat by noise and other inconsistencies such as motion and metal artifacts. Interpolating noisy data generally gives rise to a rather rough and jagged fit curve. In this situation, it may be preferable to fit a curve that balances consideration of agreement with the measured points and overall smoothness. One way to quantify these requirements is as follows. Given samples $Y_k=g(z_k)$ of a curve $g(z)$ sampled at points $z_k, k=0, \ldots NR-1$, the fit curve may be defined to be the minimizer of the following objective function:

$$\Phi(g) = \sum_{k=0}^{NR-1} W_k [y_k - \hat{g}(z_k)]^2 + \alpha \int_{z_a}^{z_b} [\hat{g}''(z_k)]^2 dz, \quad (12)$$

where $z_a$ and $z_b$ are the endpoints of the interval being considered, " denotes the second derivative, $W_k$ are weights, and $\alpha$ is a smoothing parameter that governs the tradeoff between fidelity to the data, measured by the first term, and smoothness, measured by the second. It can be shown that the minimizers of this objective function are always natural cubic splines.

The weights $W_k$ affect the relative influence each measured point has on the shape of the fit curve, and they should, in principle, be chosen to reflect the relative certainty of each measurement. An optimal choice would be the inverse of the variance of each measurement, and while this is not in general known a priori, it can be estimated from the measurements themselves. Alternatively, an unweighted formulation, in which all the weights are set to 1, may be used. The smoothing parameter greatly influences the appearance of the fit curve, with a small value of $\beta$ leading to a less smooth curve passing closer to the measured data values, and a large value of $\beta$ leading to a smoother curve with less regard for agreement with the data. The value of $\beta$ may be set a priori based on expected noise levels, or it may be determined automatically from the data by a procedure known as GCV. In the context of helical CT, it would be wise to use the same value of $\alpha$ at each $\gamma_i$ and $\beta_j$.

Fitting smoothing splines minimizing Eq. 12 to the longitudinal samples at each $\gamma_i$ and $\beta_j$ again entails determining sets of spline coefficients. The most efficient way of doing this depends on how the weights $W_k$ are chosen. If the same weights are used at each $\gamma_i$ and $\beta_j$ or the weights are all set to 1, then the same algorithm discussed above should be used, for the matrices A, B, C, and D will again be the same at all $\gamma_i$ and $\beta_j$, although, of course, they will not be the same as in the interpolating case. Conversely, if the weights are different at each $\gamma_i$ and $\beta_j$, for instance if they are determined from the data, then the matrices A, B, C, and D will also differ at each $\gamma_i$ and $\beta_j$. In that situation, there are more efficient ways to proceed that entail manipulating the data directly while exploiting the banded properties of the matrices that enforce the continuity constraints without ever directly calculating A, B, C, and D.

An integral spline model may be used for resolution enhancement in spline-based approach. In addition to odd-order (cubic) smoothing splines, even-order smoothing splines may be provided that explicitly account for the finite collimation width of the detector elements. For all of the spline-based approaches discussed so far, it has been implicitly assumed that the measured longitudinal data at each $\gamma_i$ and $\beta_j$ were noise-corrupted point samples $p(\gamma_i,\beta_j,z_k)$ of the underlying continuous curves of interest $p(\gamma_i,\beta_j,z)$. A more accurate model, however, would reflect the fact that each measured sample is, in fact, an integral of the curve $p(\gamma_i,\beta_j,z)$ over the width of the detector collimation, still corrupted by noise. We would then wish to fit a curve whose integral over appropriate intervals agreed with the detector measurements, yet which still maintained a desirable degree of smoothness. This integral model can be easily incorporated into the curve-fitting formalism we have been describing.

Working, for notational simplicity, in terms of a 1D function, imagine we have a curve g(z) of which we have samples $y_k$, k=0, . . . , NR−1, given by $$y_k = \int_{z_k^l}^{z_k^r} g(z)\,dz + \varepsilon_k, \qquad (13)$$

where the common measurement intervals $$(z_k^l, z_k^r)$$

are assumed not to overlap $$(z_k^r \leq z_{k+1}^l),$$

but may be non-adjacent $$(z_k^r < z_{k+1}^l),$$

and where $\varepsilon_k$ is additive noise. The natural extension of the curve-fitting objective of Eq. 12 to this situation is $$\Phi(g) = \sum_{k=0}^{NR-1} W_k \left[ y_k - \int_{z_k^l}^{z_k^r} \hat{g}(z)\,dz \right]^2 + \alpha \int_{z_a}^{z_b} [\hat{g}''(z)]^2\,dz. \qquad (14)$$

It can be shown that the minimizer of this objective is a curve that is a fourth-order spline on the measurement intervals $$(z_k^l, z_k^r)$$

and a cubic spline in the gaps $$(z_k^r \leq z_{k+1}^l)$$

between intervals. Again the imposition of various continuity and end conditions give rise to a system of equations involving banded matrices that can be solved very efficiently for the spline coefficients.

This technique applies quite naturally to helical CT, although the restriction that the measurement intervals $$(z_k^l, z_k^r)$$

not overlap prevents it from being applied directly to single-slice acquisitions with pitch less than 1 or to multi-slice acquisitions with pitch less than N. As in the point-sample model, if the weights $W_k$ differ at each $\gamma_i$ and $\beta_j$, one needs to solve a system of equations at each $\gamma_i$ and $\beta_j$ in order to find the spline coefficients that may be used for evaluating the underlying curve $p(\gamma_i,\beta_j,z)$ at arbitrary z. If the weights are the same at each $\gamma_i$ and $\beta_j$, or are simply all set to 1, then a single set of matrices directly relating the spline coefficients to the measured data may be determined. This approach may be implemented and an assessment made of whether it affords significant resolution improvements over the point-sample model without unduly compromising noise properties. More importantly, the extension of the formalism to the situation where the measurement intervals are permitted to overlap, which would allow it to be applied to lower pitches and to the incorporation of redundant fan-beam information may be investigated. Again, the properties of the approach for a variety of choices of the smoothing parameter $\beta$ may be investigated and may also extend the GCV formalism for the automatic determination of $\beta$ from the data in this context.

This approach may also be extended to the explicit cone-beam geometry. All of the discussion above regarding the occasional need to account explicitly for the cone-beam geometry in multi-slice helical CT and the difficulties of doing so apply to the spline-based approach as well as to the Fourier-based approach. Our strategy here is the same as in that case: modifying and extending the Defrise algorithm to convert the tilted fan-beam projections into transverse fan-beam projections, after which we can apply the spline-based approach in the usual way.

Figure 11:
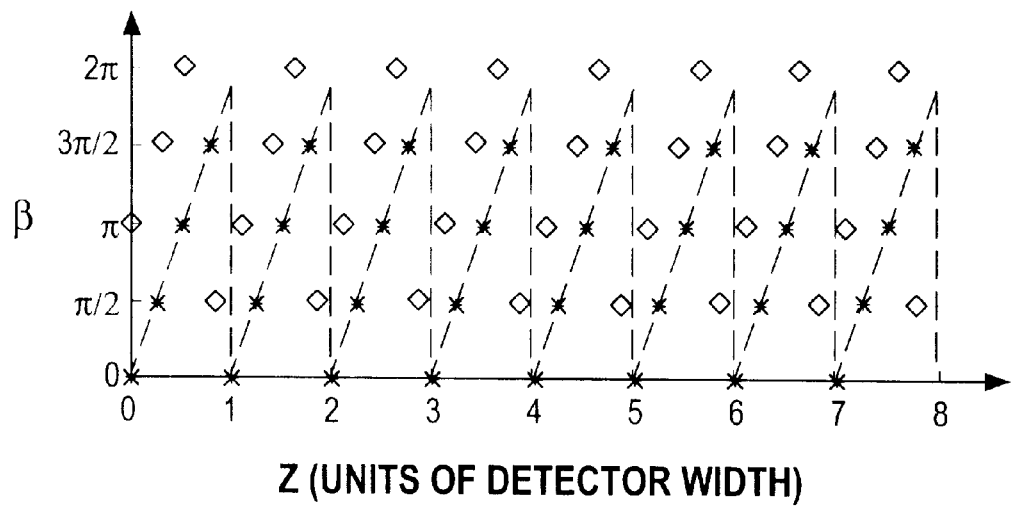
FIG. 11 illustrates a sampling pattern after augmentation with redundant data by the system of FIG. 1.

Optimal methods may be provided for the exploitation of redundant fan-beam information. The first area to be considered is redundant information. Approaches may be provided for exploiting the redundant information inherent in fan-beam acquisitions to improve the accuracy of the longitudinal interpolation. In determining the value of a projection ray are arbitrary z for a given $\gamma_i$ and $\beta_j$, the Fourier- and spline-based interpolation approaches described so far have only made use of the directly sampled projection lines at the same $\gamma_i$ and $\beta_j$. However, owing to the redundancy of fan-beam data acquired over $2\pi$, the helical CT dataset contains a second set of oppositely oriented rays corresponding to essentially the same projection lines. In the continuous case, the redundancy is described by the relationship $$p(-\gamma,\beta,z)=p(\gamma,\beta\pm\pi-2\gamma,z), \qquad (15)$$

where the sign of $\pi$ on the right hand side is chosen to keep the angle between 0 and $2\pi$. In the discrete case, this means that, for a fixed $\gamma_i$, the sampling pattern in the $\{\beta,z\}$ subspace can be augmented by picking up each sample $\{\beta_j,z_k\}$ in the {β,z} subspace for −γ and placing it at $(\beta_j \pm \pi - 2\gamma_i, z_k)$. FIG. 11 illustrate a typical augmented sampling pattern that might arise in single-slice helical CT. The same redundancy can, of course, be exploited to augment the sampling patterns in multi-slice helical CT.

Figure 12:
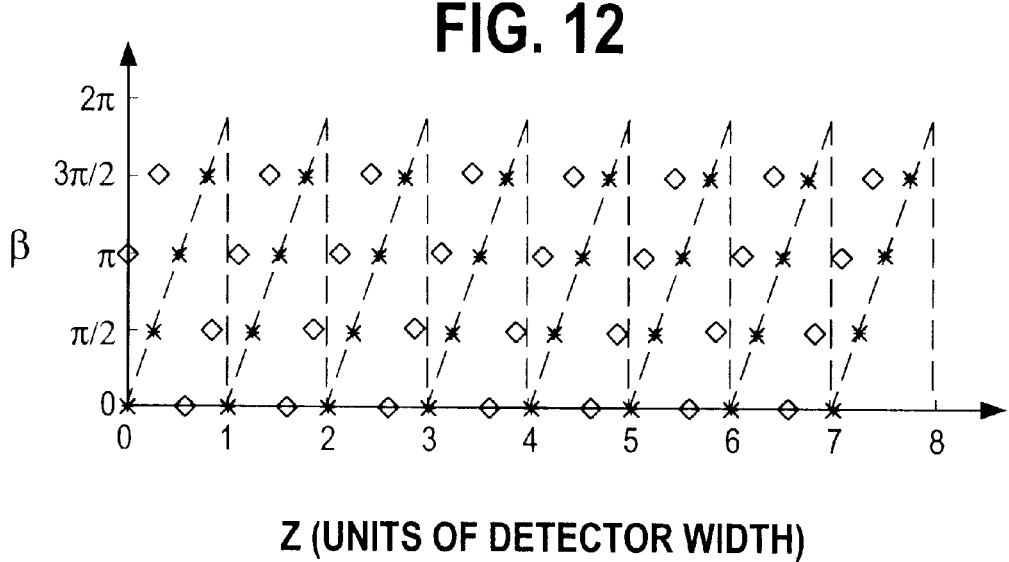
FIG. 12 illustrates an augmented sampling pattern after shifting redundant data by the system of FIG. 1.
Figure 13:
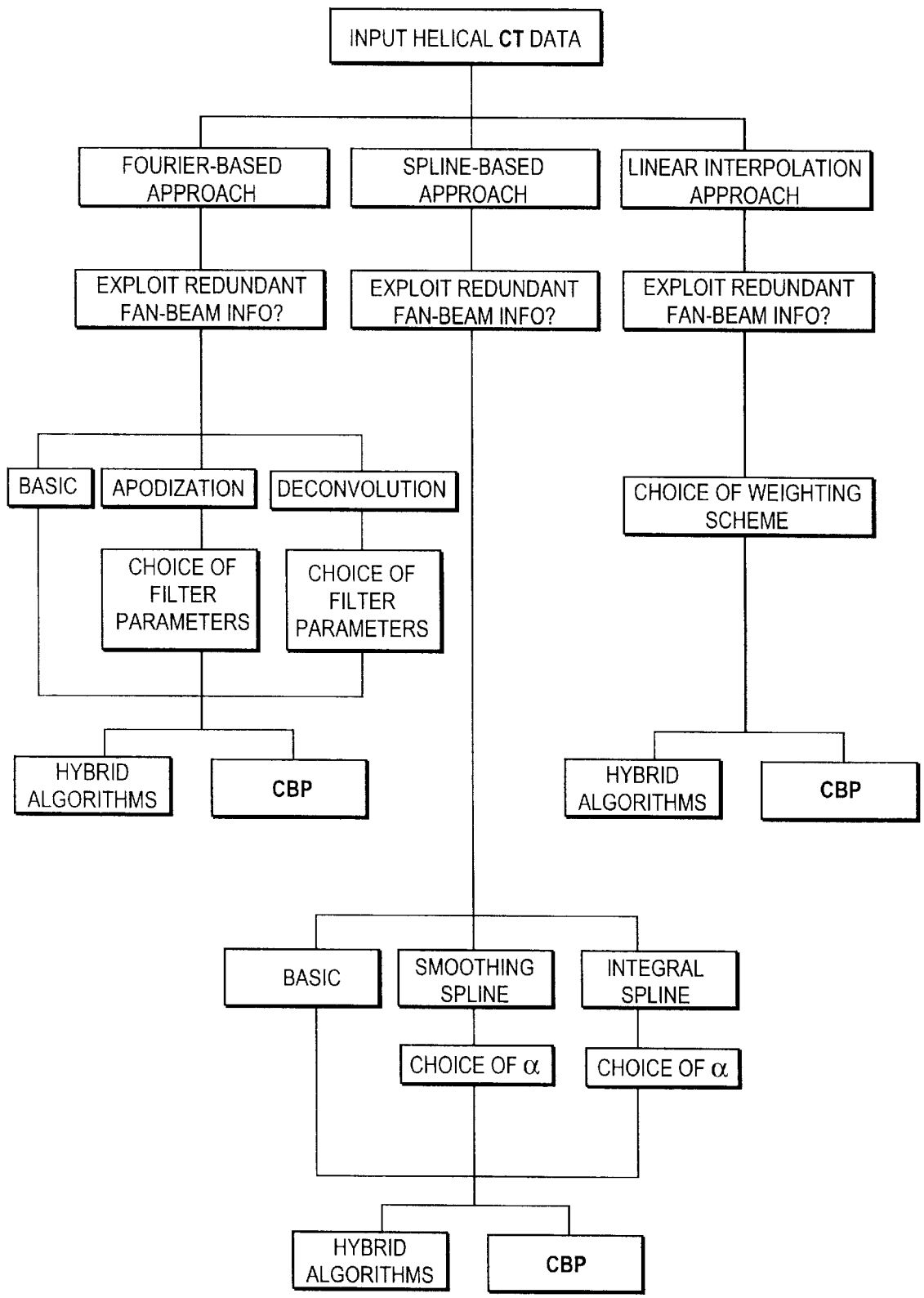
FIG. 13 is a flow chart illustrating method steps that may be used by the system of FIG. 1.

Direct and redundant samples in angular coordinates may be aligned. Two issues arise when exploiting this augmented sampling pattern. The first is that the set of discrete β values at which the additional samples lie is not necessarily coincident with the set of discrete β values at which the direct samples is known. The strategy for dealing with this misalignment will be to shift the samples along the diagonal trajectory lines so that they align with the directly measured samples. FIG. 11 might make it seem as if this should be done along each such line independently; however, it must be remembered that these lines represent a continuous helix, and thus the entire set of redundant samples can be treated as samples of a single 1D function. In the Fourier-based approach we will apply the Fourier-shift strategy to the set of samples, whereas in the spline-based approach we will fit a spline and resample at the appropriate discrete points. A typical sampling pattern resulting from this step is shown in FIG. 12. This strategy can also be applied to the more complex sampling patterns encountered in multi-slice helical CT.

An augmented sampling grid may also be used. The second issue, which becomes clear upon inspection of FIG. 12, is that, with the addition of the redundant data, the single-slice helical CT sampling pattern in z at each $\gamma_i$ and $\beta_j$ is no longer uniform. This issue is easy to overcome, for the non-uniform sampling can simply be accomodated by invoking the multi-slice approach in both the Fourier-based and spline-based approaches. A more subtle issue arises in some instances when the redundant data are used in the genuine multi-slice case, because to certain combinations of pitches and $\gamma_i$ it may be the case that the complementary information from one detector row replicates the direct sampling of another detector row. In this situation, the linear equations (see Eq. 7) that arise in the multi-slice formalism become singular. Strategies for dealing with this situation may also be provided, which may simply entail disregarding or appropriately normalizing the redundant information for those ill-behaved combinations of pitch and $\gamma_i$.

Novel fan-beam reconstruction algorithms may also be provided. The implementation of the hybrid algorithms described above is quite straightforward. The goal is to estimate samples of a 2D parallel-beam sinogram $p(\xi,\theta)$ where ξ is the detector-bin index and θ the projection angle, given samples of a fan-beam sinogram $q(\gamma,\beta)$. One first performs a 1D FFT with respect to β in order to obtain the Fourier series coefficients $Q_k(\gamma)$ of the fan-beam sinogram, where the integer k is the angular frequency index. It can be shown that the following relationships exist between these coefficients $Q_k(\gamma)$ and the Fourier series coefficients $P_k(\gamma)$ of the parallel-beam sinogram:

$$P_k(\xi) = \eta^k Q_k(\gamma) \text{ and } P_k(\xi) = (-1)^k \eta^{-k} Q_k(-\gamma), \quad (16)$$

where $\eta = e^{-j\gamma}$. In the presence of noise, these two estimates provide statistically complementary information and are thus combined in a weighted sum:

$$P_k^{(\omega)}(\xi) = \omega(\gamma,k)[\eta^k Q_k(\gamma)] + (1-\omega(\gamma,k))[(-1)^k \eta^{-k} Q_k(-\gamma)], \quad (17)$$

where the weight $\omega(\gamma,k)$ can be a generally complex function of γ and k, although in practice for CT measurements the constant 0.5 is usually optimal. Due to the nonlinear relationship between ξ and γ, the desired points ξ at which $P_k^{(\omega)}(\xi)$ is to be calculated do not coincide, in general, with the values of γ at which $Q_k(\gamma)$ and $Q_k(-\gamma)$ are measured. Interpolation is thus required, and because for typical CT measurements the sampling density of the $Q_k(\gamma)$ in the {γ} subspace is quite high, linear interpolation usually suffices, although for maximal accuracy spline interpolation may be desirable. One can then obtain the estimated parallel-beam sinogram $p^{(\omega)}(\xi,\theta)$ from the calculated $P_k^{(\omega)}(\xi)$ by taking an inverse FFT with respect to k. The image may then be reconstructed from $p^{(\omega)}(\xi,\theta)$ by FBP.

The performance of the hybrid algorithms may be easily evaluated. In addition to examining the performance of the hybrid algorithms in the context of helical reconstruction, extensive studies may be made of their performance and physical properties when reconstructing from conventional 2D fan-beam sinograms. Specifically, the noise characteristics-variance, covariance, and SNR-of images reconstructed by use of the hybrid algorithms may be evaluated and compared to those reconstructed by CPB. In doing so, a variety of noise models may be employed, including stationary Gaussian, nonstationary Gaussian, and Poisson noise. The resolution achievable with the hybrid algorithms may be examined and compared to CBP by comparing the point-spread function and associated MTF obtained when imaging a point source.

Optimal short-scan hybrid algorithms may be provided. The hybrid algorithms as described above implicitly assume that the fan-beam data span the angular range [0, 2π]; this is necessary for the computation of the Fourier series coefficients $Q_k(\gamma)$. However, it is well known that fan-beam data in the angular range $[0, \pi+2\gamma_m]$ are actually sufficient for reconstruction. Therefore, short-scan hybrid algorithms may be provided that take advantage of this statistically complementary information for variance reduction while still employing the novel rebinning strategy described above. The approach is based on the design of novel data-weighting functions that permit computation of the Fourier series coefficients $Q_k(\gamma)$ despite the truncated angular range. Short-scan algorithms may be implemented and used to evaluate their noise and resolution properties. It is expected that the short-scan algorithms will share the advantages that the regular hybrid algorithms have over CBP.

A specific embodiment of a method and apparatus for reconstructing helical CT according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method of reconstructing a set of CT images from helical CT data, such method comprising the steps of:
    receiving the helical CT data;
    generating a set of fan-beam sinograms at equally spaced longitudinal positions; and
    estimating a set of parallel-beam sinograms from the generated set of fan-beam sinograms; and
    reconstructing the CT images using a parallel beam reconstruction algorithm.

2. The method of reconstructing the set of CT images as in claim 1 wherein the step of generating the set of fan-beam sinograms further comprises translating the longitudinal sampling grid of the helical CT data at each view angle to conform to a predetermined set of equally spaced longitudinal positions.

3. The method of reconstructing the set of CT images as in claim 2 wherein the step of translating the longitudinal sampling grid of the helical CT data further comprises using a Fourier shift theorem.

4. The method of reconstructing the set of CT images as in claim 3 wherein the step of translating the longitudinal sampling grid using the Fourier shift theorem further comprises multiplication by an apodization window.

5. The method of reconstructing the set of CT images as in claim 3 wherein the step of translating the longitudinal sampling grid using the Fourier shift theorem further comprises using Fourier-domain deconvolution techniques.

6. The method of reconstructing the set of CT images as in claim 3 wherein the step of translating the longitudinal sampling grid using the Fourier shift theorem further comprises solving a set of frequency-domain equations in the case of multiple detector rows.

7. The method of reconstructing the set of CT images as in claim 1 further comprising augmenting the received helical CT data using the redundancy of fanbeam data over a $2\pi$ data interval.

8. The method of reconstructing the set of CT images as in new claim 7 wherein use of the redundant data further comprises aligning the redundant data with the directly measured data using the Fourier shift theorem and solving a set of frequency-space equations.

9. The method of reconstructing the set of CT images as in claim 1 wherein the step of generating the set of fan-beam sinograms further comprises fitting a continuous curve to a set of longitudinal samples of the helical data.

10. The method of reconstructing the set of CT images as in claim 9 wherein the step of fitting a continuous curve further comprises fitting a spline to the helical CT data.

11. The method of reconstructing the set of CT images as in claim 10 wherein the step of fitting a spline to the helical data further comprises interpolating the data with the spline.

12. The method of reconstructing the set of CT images as in claim 10 wherein the step of fitting a spline to the helical data further comprises finding the minimizer of:

$$\Phi(g) = \sum_{k=0}^{NR-1} W_k [y_k - \hat{g}(z_k)]^2 + \alpha \int_{z_a}^{z_b} [\hat{g}''(z_k)]^2 \, dz.$$

13. The method of reconstructing the set of CT images as in claim 10 wherein the step of fitting a spline to the helical data further comprises finding the minimizer of:

$$\Phi(g) = \sum_{k=0}^{NR-1} W_k \left[ y_k - \int_{z_k^l}^{z_k^f} \hat{g}(z) \, dz \right]^2 + \alpha \int_{z_a}^{z_b} [\hat{g}''(z)]^2 \, dz.$$

14. The method of reconstructing the set of CT images as in claim 10 further comprising augmenting the received helical data using the redundancy of fanbeam data over a $2\pi$ data interval.

15. The method of reconstructing the set of CT images as in claim 9 wherein the step of fitting a continuous curve to a set of longitudinal samples of the helical data further comprises resampling the continuous curve at the equally spaced longitudinal positions.

16. Apparatus for reconstructing a set of CT images from helical CT data, such apparatus comprising:
means for receiving the helical CT data;
means for generating a set of fan-beam sinograms at equally spaced longitudinal positions; and
means for estimating a set of parallel-beam sinograms from the generated set of fan-beam sinograms; and
means for reconstructing the CT images using a parallel beam reconstruction algorithm.

17. The apparatus for reconstructing the set of CT images as in claim 16 wherein the means for generating the set of fan-beam sinograms further comprises means for translating the longitudinal sampling grid of the helical CT data at each view angle to conform to a predetermined set of equally spaced longitudinal positions.

18. The apparatus for reconstructing the set of CT images as in claim 17 wherein the means for translating the longitudinal sampling grid of the helical CT data further comprises means for using a Fourier shift theorem.

19. The apparatus for reconstructing the set of CT images as in claim 18 wherein the means for translating the longitudinal sampling grid using the Fourier shift theorem further comprises means for multiplication by an apodization window.

20. The apparatus for reconstructing the set of CT images as in claim 18 wherein the means for translating the longitudinal sampling grid using the Fourier shift theorem further comprises means for using Fourier-domain deconvolution techniques.

21. The apparatus for reconstructing the set of CT images as in claim 18 wherein the means for translating the longitudinal sampling grid using the Fourier shift theorem further comprises means for solving a set of frequency-domain equations in the case of multiple detector rows.

22. The apparatus for reconstructing the set of CT images as in claim 16 further comprising means for augmenting the received helical CT data using the redundancy of fanbeam data over a $2\pi$ data interval.

23. The apparatus for reconstructing the set of CT images as in new claim 22 wherein the means for augmenting the redundant data further comprises means for aligning the redundant data with the directly measured data using the Fourier shift theorem and solving a set of frequency-space equations.

24. The apparatus for reconstructing the set of CT images as in claim 16 wherein the means for generating the set of fan-beam sinograms further comprises means for fitting a continuous curve to a set of longitudinal samples of the helical data.

25. The apparatus for reconstructing the set of CT images as in claim 24 wherein the means for fitting a continuous curve further comprises means for fitting a spline to the helical CT data.

26. The apparatus for reconstructing the set of CT images as in claim 25 wherein the means for fitting a spline to the helical data further comprises means for interpolating the data with the spline.

27. The apparatus for reconstructing the set of CT images as in claim 25 wherein the means for fitting a spline to the helical data further comprises means for finding the minimizer of:

$$\Phi(g) = \sum_{k=0}^{NR-1} W_k [y_k - \hat{g}(z_k)]^2 + \alpha \int_{z_a}^{z_b} [\hat{g}''(z_k)]^2 \, dz.$$

28. The apparatus for reconstructing the set of CT images as in claim 25 wherein the means for fitting a spline to the helical data further comprises means for finding the minimizer of:

$$\Phi(g) = \sum_{k=0}^{NR-1} W_k \left[ y_k - \int_{z_k^I}^{z_k^T} \hat{g}(z) dz \right]^2 + \alpha \int_{z_a}^{z_b} [\hat{g}''(z)]^2 dz.$$

29. The apparatus for reconstructing the set of CT images as in claim 25 further comprising means for augmenting the received helical data using the redundancy of fanbeam data over a $2\pi$ data interval.

30. The apparatus for reconstructing the set of CT images as in claim 24 wherein the means for fitting a continuous curve to a set of longitudinal samples of the helical data further comprises means for resampling the continuous curve at the equally spaced longitudinal positions.

31. Apparatus for reconstructing a set of CT images from helical CT data, such apparatus comprising:
  a memory adapted to receive the helical CT data;
  a sinogram processor adapted to generate a set of fan-beam sinograms at equally spaced longitudinal positions; and
  an estimator processor adapted to estimate a set of parallel-beam sinograms from the generated set of fan-beam sinograms; and
  a reconstruction processor adapted to reconstruct the CT images using a parallel beam reconstruction algorithm.

32. The apparatus for reconstructing the set of CT images as in claim 31 wherein the sinogram processor further comprises a translation processor adapted to translate the longitudinal sampling grid of the helical CT data at each view angle to conform to a predetermined set of equally spaced longitudinal positions.

33. The apparatus for reconstructing the set of CT images as in claim 32 wherein the translation processor further comprises a Fourier processor adapted to use a Fourier shift theorem.

34. The apparatus for reconstructing the set of CT images as in claim 33 wherein the translation processor further comprises an apodization processor adapted to multipliply the sampling grid by an apodization window.

35. The apparatus for reconstructing the set of CT images as in claim 33 wherein the translation processor further comprises a deconvolution processor adapted to use Fourier-domain deconvolution techniques.

36. The apparatus for reconstructing the set of CT images as in claim 33 wherein the translation processor further comprises a frequency-domain processor adapted to solve a set of frequency-domain equations in the case of multiple detector rows.

37. The apparatus for reconstructing the set of CT images as in claim 31 wherein the sinogram processor further comprises a curve fitting processor adapted to fit a continuous curve to a set of longitudinal samples of the helical data.

38. The apparatus for reconstructing the set of CT images as in claim 37 wherein the curve fitting processor further comprises a spline procesor adapted to fit a spline to the helical CT data.

39. The apparatus for reconstructing the set of CT images as in claim 38 wherein the spline processor further comprises an interpolating processor adapted to interpolate the data with the spline.

40. The apparatus for reconstructing the set of CT images as in claim 38 wherein the spline processor further comprises a first arithmetic unit adapted to find the minimizer of:

$$\Phi(g) = \sum_{k=0}^{NR-1} W_k [y_k - \hat{g}(z_k)]^2 + \alpha \int_{z_a}^{z_b} [\hat{g}''(z_k)]^2 dz.$$

41. The apparatus for reconstructing the set of CT images as in claim 38 wherein the spline processor further comprises a second arithmetic unit adapted to find the minimizer of:

$$\Phi(g) = \sum_{k=0}^{NR-1} W_k \left[ y_k - \int_{z_k^I}^{z_k^T} \hat{g}(z) dz \right]^2 + \alpha \int_{z_a}^{z_b} [\hat{g}''(z)]^2 dz.$$

42. The apparatus for reconstructing the set of CT images as in claim 37 wherein the curve fitting processor further comprises a resampling processor adapted to resample the continuous curve at the equally spaced longitudinal positions.

* * * * *